(12) United States Patent
Schmülling et al.

(10) Patent No.: US 9,422,570 B2
(45) Date of Patent: Aug. 23, 2016

(54) DISRUPTION OF AHP6 GENE LEADS TO PLANTS WITH IMPROVED SEED YIELD

(76) Inventors: Thomas Schmülling, Berlin (DE); Tomas Werner, Berlin (DE)

( * ) Notice: Subject to any disclaimer, the term of this patent is extended or adjusted under 35 U.S.C. 154(b) by 297 days.

(21) Appl. No.: 13/995,065

(22) PCT Filed: Dec. 16, 2011

(86) PCT No.: PCT/EP2011/073058
§ 371 (c)(1),
(2), (4) Date: Jun. 17, 2013

(87) PCT Pub. No.: WO2012/084715
PCT Pub. Date: Jun. 28, 2012

(65) Prior Publication Data
US 2013/0269062 A1    Oct. 10, 2013

(30) Foreign Application Priority Data
Dec. 20, 2010 (EP) .................................... 10196018

(51) Int. Cl.
*C12N 15/05* (2006.01)
*C07K 14/415* (2006.01)
*C12N 15/82* (2006.01)

(52) U.S. Cl.
CPC .......... *C12N 15/8261* (2013.01); *C07K 14/415* (2013.01); *C12N 15/8295* (2013.01)

(58) Field of Classification Search
None
See application file for complete search history.

(56) References Cited

U.S. PATENT DOCUMENTS

2006/0123507 A1 *   6/2006   Ashikari et al.   ............... 800/278

FOREIGN PATENT DOCUMENTS

EP    11807665    1/2016

OTHER PUBLICATIONS

Mahonen et al. (Science Jan. 6, 2006 vol. 311 94-98).*
Gu et al. (J Plant Growth Regul (2010) 29:428-440).*
Hutchison et al. (The Plant Cell, vol. 18, 3073-3087, Nov. 2006).*
Mahonen et al. (Science Jan. 6, 2006 vol. 311 94-98) Supplemental materials.*

* cited by examiner

*Primary Examiner* — Elizabeth McElwain
*Assistant Examiner* — Charles Logsdon
(74) *Attorney, Agent, or Firm* — VLP Law Group LLP; Kent H. Cheng

(57) ABSTRACT

The present invention is directed to a method for increasing seed yield in a plant, the method comprising disruption of endogenous AHP6 gene in cells of the plant, wherein said disruption inhibits expression and/or activity of a product of said endogenous AHP6 gene compared to a corresponding control plant lacking such a disruption.

9 Claims, 4 Drawing Sheets

DISRUPTION OF AHP6 GENE LEADS TO PLANTS WITH IMPROVED SEED YIELD

PRIORITY CLAIM

This is a U.S. national stage of application No. PCT/EP2011/073058, filed on Dec. 16, 2011. Priority is claimed on the following application: Application No.: EP 10 196 018.5, filed: Dec. 20, 2010, the content of which is incorporated here by reference.

SEQUENCE LISTING

The instant application contains a Sequence Listing which has been submitted in ASCII format via EFS-Web and is hereby incorporated by reference in its entirety. Said ASCII copy is named P08450WO.txt and is 39,299 bytes in size.

BACKGROUND OF THE INVENTION

In order to be able to supply a continuously growing population with food and other plant-derived products, people have always been interested in improving the productivity in agriculture.

The productivity of a plant can be influenced in various different ways, e.g. by improving plant growth characteristics or by delaying leaf senescence. There are many mechanisms and pathways known which are involved in plant growth and development.

Cytokinin is a plant hormone that plays positive and negative regulatory roles in many aspects of plant growth and development. It stimulates the formation and activity of shoot meristems, is able to establish sink tissues, retard leaf senescence, inhibits root growth and branching, and plays a role in seed germination and stress responses (Mok, D. W. S. & Mok, M. C. (2001) Ann. Rev. Plant Physiol. Mol. Bio. 52, 89-1 18). Analysis of cytokinin-deficient plants has shown that cytokinin plays opposite roles in shoot and root meristems and suggests that the hormone has an essential function in quantitative control of organ growth (Werner T, Motyka V, Laucou V, Smets R, Van Onckelen H, Schmülling T, Plant Cell 2003, 15(11):2532-50; Werner T, Motyka V, Strnad M, Schmülling T, Proc Natl Acad Sci USA 2001, 98(18):10487-92).

It has been shown that cytokinin oxidases/dehydrogenases (CKX) are an important factor to regulate the homeostasis of the plant hormone cytokinin. The genome of *Arabidopsis* encodes seven CKX genes, which have distinct expression domains (Werner et al., 2001; Werner et al., 2003). The CKX proteins differ in their subcellular localization and biochemical features (Werner et al., 2003). Overexpression of individual CKX genes established cytokinin-deficient plants and revealed that cytokinin is a positive regulator of the shoot meristem activity and a negative regulator of root meristem activity.

Recently it was shown that in a rice plant inhibition of the function of a particular CKX gene, the rice orthologue to CKX3 of *Arabidopsis thaliana*, has led to an increase in particle-bearing number of said rice plant (see US 2006/0123507 A1).

Although these results are promising, there remains a need for further improving the productivity of plants.

It is an object of the present invention to provide means and methods suitable to improve productivity of plants.

This object is achieved by the present invention as set out in detail below.

SUMMARY OF THE INVENTION

The present invention provides a method for increasing seed yield in a plant, the method comprising disruption of endogenous AHP6 gene in cells of the plant, wherein said disruption inhibits expression and/or activity of a product of said endogenous AHP6 gene compared to a corresponding control plant lacking such a disruption.

Surprisingly it has been found that in a plant disruption of the AHP6 gene leads to plants with a seed yield that is higher than that of a plant lacking such disruption. Whereas single disruption of AHP6 already leads to a significant increase in seed yield, the simultaneous disruption of AHP6 together with at least one CKX gene leads to a remarkable further increase in seed yield compared to wild type and single disruptions of CKX genes. Most significant increase in seed yield was observed for a simultaneous disruption of AHP6, CKX3 and CKX5. Even more surprisingly, it has been found that simultaneous stable disruption of AHP6 and at least one CKX gene leads to plants with even more improved productivity. It appears that disruption of the endogenous AHP6 gene in a plant with an increased cytokinin status is particularly effective. An increase in cytokinin status is observed when the plant shows a phenotype which is usually associated with the presence of an increased amount of cytokinin. Such an increased cytokinin status can be the result of a simultaneous disruption of AHP6 together with at least one endogenous CKX gene of the plant, e.g. a simultaneous disruption of AHP6 together with at least two different endogenous CKX genes. However, an increased cytokinin status can also be the result of other alterations or manipulations such as e.g. mutations in genes involved in synthesis of cytokinins or mutations in cytokinin receptors. Another option is to influence the cytokinin status of a plant by administration of chemical compounds. There are compounds known that lead to an increased cytokinin status.

In a first aspect, the present invention is directed to a method for increasing seed yield in a plant, the method comprising disruption of endogenous AHP6 gene in cells of the plant, wherein said disruption inhibits expression and/or activity of a product of said endogenous AHP6 gene compared to a corresponding control plant lacking such a disruption.

In a second aspect, the invention refers to a use of the method of the invention for increasing seed yield in a plant and the progeny derived therefrom and/or for production of a non-naturally occurring plant with increased seed yield.

In a third aspect, the present invention provides a non-naturally occurring plant comprising a disruption in an endogenous AHP6 gene and a disruption in at least one endogenous CKX gene.

The present invention is also directed to an isolated plant cell or a non-naturally occurring plant obtainable or obtained by one of the methods of the invention.

Unless defined otherwise, all technical and scientific terms used herein have the same meaning as commonly understood by one of ordinary skill in the art to which the invention pertains. In describing and claiming the present invention, the following terminology will be used in accordance with the definitions set out below.

As used in this specification and the appended claims, the singular forms "a", "an" and "the" include singular and plural referents unless the content clearly dictates otherwise. Thus, for example, reference to "a cell" includes one cell and a combination of two or more cells, and the like.

In the method of the present invention seed yield of a plant is increased.

The term "plant" refers generically to any of: whole plants, plant parts or organs (e.g. leaves, stems, roots, etc.), shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat), fruit (the mature ovary), plant tissue (e.g. vascular tissue, ground tissue, and the like), tissue culture callus, and plant cells (e.g. guard cells, egg cells, trichomes and the like), and progeny of same. The term "plant" generally means all those organisms which are capable of photosynthesis. Included as plant within the scope of the invention are all genera and species of the higher and lower plants of the plant kingdom. Mature plants means plants at any developmental stage beyond the seedling. Seedling means a young immature plant in an early developmental stage. The plants of the invention may be annual, perennial, monocotyledonous and/or dicotyledonous plants. In particular, the plants of the invention can be plants of the following plant family: Brassicaceae, in particular to plants of the genera *Brassica* and *Arabidopsis*.

Plant cell, as used herein, further includes, without limitation, cells obtained from or found in a plant or a part thereof: seeds, cultures, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues.

As used herein, the term "non-naturally occurring" when used in reference to a plant, means a plant with a genome that has been modified by man. A transgenic plant, for example, is a non-naturally occurring plant. A transgenic plant may contain e.g. an exogenous nucleic acid molecule, e.g., a chimeric gene comprising a transcribed region which when transcribed yields a biologically active RNA molecule capable of reducing the expression of an endogenous gene, such as an AHP6 gene according to the invention, and, therefore, has been genetically modified by man. In addition, a plant that contains a mutation in an endogenous gene, for example, a mutation in an endogenous AHP6 gene, (e.g. in a regulatory element or in the coding sequence) as a result of an exposure to a mutagenic agent is also considered a non-naturally plant, since it has been genetically modified by man. Furthermore, a plant of a particular species, such as e.g. *Brassica napus* or other members of the family of Brassicaceae, that contains a mutation in an endogenous gene, for example, in an endogenous AHP6 gene, that in nature does not occur in that particular plant species, as a result of, for example, directed breeding processes, such as marker-assisted breeding and selection or introgression, with a plant of the same or another species of that plant is also considered a non-naturally occurring plant. In contrast, a plant containing only spontaneous or naturally occurring mutations, i.e. a plant that has not been genetically modified by man, is not a "non-naturally occurring plant" as defined herein and, therefore, is not encompassed within the invention. One skilled in the art understands that, while a non-naturally occurring plant typically has a nucleotide sequence that is altered as compared to a naturally occurring plant, a non-naturally occurring plant also can be genetically modified by man without altering its nucleotide sequence, for example, by modifying its methylation pattern.

The term "transgenic" refers to a plant that has incorporated nucleic acid sequences, including but not limited to genes, polynucleotides, DNA, RNA, etc., and/or alterations thereto (e.g. mutations, point mutations or the like), which have been introduced into a plant compared to a non-introduced plant by processes which are not essentially biological processes for the production of plants. Thus, the term "transgenic plant" encompasses not only plants comprising non-endogenous nucleic acids, but explicitly refers also to plants that bear mutations in an endogenous gene, e.g. point mutations, which have been introduced into said transgenic plant compared to a non-introduced plant by processes which are not essentially biological processes for the production of plants.

In the method of the invention seed yield in a plant is increased by disruption of endogenous AHP6 gene.

The term "gene" or "gene sequence" is used broadly to refer to any nucleic acid associated with a biological function. Genes typically include coding sequences and/or the regulatory sequences required for expression of such coding sequences. The term "gene" applies to a specific genomic sequence, as well as to a cDNA or an mRNA encoded by that genomic sequence. Genes also include non-expressed nucleic acid segments that, for example, form recognition sequences for other proteins. Non-expressed regulatory sequences include promoters and enhancers, to which regulatory proteins such as transcription factors bind, resulting in transcription of adjacent or nearby sequences.

The term "endogenous" relates to any gene or nucleic acid sequence that is already present in a given wild type cell or organism like e.g. a plant. The term "exogenous" relates to any gene or nucleic acid sequences that is not endogenous.

The AHP6 gene encodes for a AHP6 protein first described in *Arabidopsis thaliana*, also called *Arabidopsis* Histidine Phosphotransfer Protein 6. AHP6 protein is a member of the structural family of histidine phosphotransfer kinase/transferase proteins. However, AHP6 protein lacks the histidine residue which is required for phosphotransfer present in the other AHPs and which is conserved in the family of histidine phosphotransfer kinase/transferase. Instead of said histidine residue AHP6 exhibits an Asparagine residue at position Asn83 of AHP6a with SEQ ID No. 1. For the purpose of the present invention, the term "AHP6 protein" can refer to a protein that, e.g.:

is a member of the structural family of histidine phosphotransfer kinase/transferase proteins; and/or lacks a histidine at a position corresponding to the position Asn83 of SEQ ID No. 1; and/or exhibits essentially the same function as AHP6 protein with SEQ ID No. 1 or 12; and/or comprises an amino acid sequence having a sequence identity of at least 70%, at least 80%, at least 90% or at least 95% when compared to the entire amino acid sequence of SEQ ID No. 1 or 12.

An AHP6 protein exhibits essentially the same function as the AHP6 protein with SEQ ID No. 1 or 12, when said protein exhibits at least 50%, at least 70% or at least 90% of the activity of AHP6 protein of *Arabidopsis thaliana* with SEQ ID No. 1 or 12 when measured in a biochemical in vitro test for AHP6 protein function. A suitable biochemical in vitro test for AHP6 protein function is described in Mähönen et al. "Cytokinin signaling and its inhibitor AHP6 regulate cell fate during vascular development", *Science* 2006, 311, 94-98. As described by Mähönen et al. (2006), AHP6 protein does not appear to have phosphotransfer activity and acts as an inhibitor of cytokinin signaling by interacting with the phosphorelay machinery.

The AHP6 protein of *Arabidopsis thaliana* exists in two alternatively spliced forms, namely AHP6a and AHP6b, whereas the two splice forms differ in the length of the first exons. As used herein and if not denoted otherwise, the term "AHP6 protein" refers to both spliced forms AHP6a and AHP6b. The AHP6 protein of *Arabidopsis thaliana* comprises an amino acid sequence of SEQ ID No. 1 for AHP6a or of SEQ ID No. 12 for AHP6b, the genomic sequence of the AHP6 gene of *Arabidopsis thaliana* comprises the nucleic acid sequence of SEQ ID No. 2, the coding sequence of AHP6 gene of *Arabidopsis thaliana* comprises the nucleic acid sequence of SEQ ID No. 3 for AHP6a protein and SEQ ID No. 13 for AHP6b and the cDNA of the AHP6 gene of *Arabidopsis thaliana* comprises the nucleic acid sequence with SEQ ID No. 4 for AHP6a and SEQ ID NO. 14 for AHP6b.

The endogenous AHP6 gene may comprise or consist of:
(a) a nucleic acid encoding an AHP6 protein comprising the amino acid sequence of SEQ ID No. 1, 12 or an orthologue thereof;
(b) a nucleic acid encoding an AHP6 protein comprising an amino acid sequence having a sequence identity of at least 70%, at least 80%, at least 90% or at least 95% when compared to the entire amino acid sequence of SEQ ID No. 1 or 12;
(c) a nucleic acid comprising the nucleic acid sequence of SEQ ID No. 2, 3, 4, 13 or 14;
(d) a nucleic acid comprising a nucleic acid sequence having a sequence identity of at least 90% through the entire nucleic acid sequence of SEQ ID No. 2, 3, 4, 13 or 14; or
(e) a nucleic acid hybridizing under stringent conditions to one of the nucleic acid sequences defined under (a), (b), (c) and/or (d).

The term "nucleic acid" or "polynucleotide" is generally used in its art-recognized meaning to refer to a ribose nucleic acid (RNA) or deoxyribose nucleic acid (DNA) polymer, or analog thereof, e.g., a nucleotide polymer comprising modifications of the nucleotides, a peptide nucleic acid, or the like. In certain applications, the nucleic acid can be a polymer that includes multiple monomer types, e.g., both RNA and DNA subunits. A nucleic acid can be, e.g., a chromosome or chromosomal segment, a vector (e.g., an expression vector), an expression cassette, a naked DNA or RNA polymer, the product of a polymerase chain reaction (PCR), an oligonucleotide, a probe, etc. A nucleic acid can be, e.g., single-stranded and/or double-stranded. Unless otherwise indicated, a particular nucleic acid sequence of the invention optionally comprises or encodes complementary sequences, in addition to any sequence explicitly indicated.

The term "polynucleotide sequence", "nucleic acid sequence", "nucleic acid" or "nucleotide sequence" refers to a contiguous sequence of nucleotides in a single nucleic acid or to a representation, e.g., a character string, thereof. That is, a "polynucleotide sequence" is a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

The term "subsequence" or "fragment" is any portion of an entire sequence.

The term "orthologue" as used herein refers to a gene from a species, e.g. different from *Arabidopsis thaliana*, that shows highest similarity, i.e. highest sequence identity, to the specified gene of *Arabidopsis thaliana* and/or that encodes for a protein exhibiting essentially the same function as the specified gene of *Arabidopsis thaliana* because both genes originated from a common ancestor. The term "orthologue" may denote an endogenous gene encoding for a protein having essentially the same function and comprising a sequence (polypeptide or nucleic acid) with at least 70%, at least 80%, at least 85%, at least 90%, at least 95%, or at least 99% sequence identity to a given sequence the respective orthologue refers to, e.g. over the whole sequence length. In particular the term "orthologue" may denote an endogenous gene, which is derived from a species different from *Arabidopsis thaliana*, encoding for a protein with essentially the same function and comprising a sequence with at least 70%, at least 80%, at least 85%, at least 90%, at least 95%, or at least 99% sequence identity to a given sequence of *Arabidopsis thaliana* the respective orthologue refers to, e.g. over the whole sequence length.

The orthologue as used herein can refer to an endogenous gene, which is derived from a species different from *Arabidopsis thaliana*, encoding for a protein with essentially the same function as and comprising an amino acid sequence with at least 70%, at least 80%, at least 85%, at least 90%, at least 95%, or at least 99% sequence identity over the whole sequence length to:
  AHP6 protein of *Arabidopsis thaliana* with SEQ ID No. 1 or 12;
  CKX1 protein of *Arabidopsis thaliana* with SEQ ID No. 5;
  CKX2 protein of *Arabidopsis thaliana* with SEQ ID No. 6;
  CKX3 protein of *Arabidopsis thaliana* with SEQ ID No. 7
  CKX4 protein of *Arabidopsis thaliana* with SEQ ID No. 8;
  CKX5 protein of *Arabidopsis thaliana* with SEQ ID No. 9;
  CKX6 protein of *Arabidopsis thaliana* with SEQ ID No. 10; and/or
  CKX7 protein of *Arabidopsis thaliana* with SEQ ID No. 11, respectively.

The orthologue of the AHP6 protein exhibits essentially the same function as the AHP6 protein of *Arabidopsis thaliana* comprising of the amino acid sequence with SEQ ID No. 1 or 12. A biochemical in vitro test for AHP6 protein function is disclosed by Mähönen et al. in "Cytokinin signaling and its inhibitor AHP6 regulate cell fate during vascular development", Science 2006, 311, 94-98. An orthologue of AHP6 protein can exhibit at least 50% of the activity of AHP6 protein of *Arabidopsis thaliana* with SEQ ID No. 1 or 12 when measured in above mentioned biochemical in vitro test, more preferably at least 70%, even more preferred at least 90%.

The orthologue of a given CKX protein of *Arabidopsis thaliana* exhibits essentially the same function as the respective CKX protein of *Arabidopsis thaliana*. The skilled person is well aware of means and methods to determine whether a given protein has cytokininoxidase/dehydrogenase activity or not and to determine the level of cytokininoxidase/dehydrogenase activity of a particular protein or probe in absolute values and/or relative to another protein or probe. There is ample guidance in the literature how a given protein can be tested for such an activity, see e.g. EC 1.5.99.12.

An orthologue of CKX1 protein may exhibit at least 50% of the activity of CKX1 protein of *Arabidopsis thaliana* with SEQ ID No. 5 when measured in above mentioned biochemical in vitro test, more preferably at least 70%, even more preferred at least 90%.

An orthologue of CKX2 protein may exhibit at least 50% of the activity of CKX2 protein of *Arabidopsis thaliana* with SEQ ID No. 6 when measured in above mentioned biochemical in vitro test, more preferably at least 70%, even more preferred at least 90%.

An orthologue of CKX3 protein may exhibit at least 50% of the activity of CKX3 protein of *Arabidopsis thaliana* with SEQ ID No. 7 when measured in above mentioned biochemical in vitro test, more preferably at least 70%, even more preferred at least 90%.

An orthologue of CKX4 protein may exhibit at least 50% of the activity of CKX4 protein of *Arabidopsis thaliana* with SEQ ID No. 8 when measured in above mentioned biochemical in vitro test, more preferably at least 70%, even more preferred at least 90%.

An orthologue of CKX5 protein may exhibit at least 50% of the activity of CKX5 protein of *Arabidopsis thaliana* with SEQ ID No. 9 when measured in above mentioned biochemical in vitro test, more preferably at least 70%, even more preferred at least 90%.

An orthologue of CKX6 protein may exhibit at least 50% of the activity of CKX6 protein of *Arabidopsis thaliana* with SEQ ID No. 10 when measured in above mentioned biochemical in vitro test, more preferably at least 70%, even more preferred at least 90%.

An orthologue of CKX7 protein may exhibit at least 50% of the activity of CKX7 protein of *Arabidopsis thaliana* with SEQ ID No. 11 when measured in above mentioned biochemical in vitro test, more preferably at least 70%, even more preferred at least 90%.

For the purpose of the present invention, sequence "identity" is objectively determined by any of a number of methods. The skilled person is well aware of these methods and can choose a suitable method without undue burden. A variety of methods for determining relationships between two or more sequences (e.g. identity, similarity and/or homology) are available and well known in the art. The methods include manual alignment, computer assisted sequence alignment and combinations thereof, for example. A number of algorithms (which are generally computer implemented) for performing sequence alignment are widely available or can be produced by one of skill. The degree of identity of one amino acid sequence or nucleotide sequence to another can be determined by following the algorithm BLAST by Karlin and Altschul (Proc. Natl. Acad. Sci. USA 90: 5873-5877, 1993). Programs such as BLASTN and BLASTX developed based on this algorithm (Altschul et al. (1990) J. Mol. Biol. 215: 403-410) may be used. To analyze a nucleotide sequence according to BLASTN based on BLAST, the parameters are set, for example, as score=100 and word length=12. On the other hand, parameters used for the analysis of amino acid sequences by the BLASTX based on BLAST include, for example, score=50 and word length=3. Default parameters of each program are used when using BLAST and Gapped BLAST program. Specific techniques for such analysis are known in the art (see www.ncbi.nim.nih.gov.).

Stringent hybridization conditions of the present invention include conditions such as: 6 M urea, 0.4% SDS, and 0.5× SSC; and those which yield a similar stringency to the conditions. Nucleic acid sequences with higher homology are expected when hybridization is performed under conditions with higher stringency, for example, 6 M urea, 0.4% SDS, and 0.1×SSC. Those nucleic acid sequences isolated under such conditions are expected to encode a protein having a high amino acid level homology with AHP6 protein (SEQ ID NO: 1). Herein, high homology means an identity of at least 50% or more, 70% or more, or 90% or more (e.g. 95% or more), through the entire amino acid sequence.

There are already three allelic, recessive mutations known that represent examples of disruptions of the endogenous AHP6 gene in the sense of the present invention. Mähönen et al. describes in "Cytokinin signaling and its inhibitor AHP6 regulate cell fate during vascular development", *Science* 2006, 311, 94-98, the mutations aph6-1, aph6-2 and aph6-3. In aph6-1 the mutation resulted in a premature stop codon in the first exon, whereas in aph6-2 the mutation is located in the first intron, 5 base pairs from the 5'-border of the AHP6b splice variant, and aph6-3 is a T-DNA insertion allele. Both aph6-1 and aph6-3 appear to represent null alleles, whereas in the aph6-2 allele only the splice variant APH6a is present.

The term "disruption" or "disrupted" as used herein means that a gene can be structurally disrupted so as to comprise at least one mutation or structural alteration such that the disrupted gene is incapable of directing the efficient expression of a full-length fully functional gene product. An endogenous gene can be disrupted in the sense of the present invention when the endogenous gene comprises one or more mutations, such as:

(a) a "missense mutation", which is a change in the nucleic acid sequence that results in the substitution of an amino acid for another amino acid;

(b) a "nonsense mutation" or "STOP codon mutation", which is a change in the nucleic acid sequence that results in the introduction of a premature STOP codon and, thus, the termination of translation (resulting in a truncated protein); plant genes contain the translation stop codons "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation.

(c) an "insertion mutation" of one or more amino acids, due to one or more codons having been added in the coding sequence of the nucleic acid;

(d) a "deletion mutation" of one or more amino acids, due to one or more codons having been deleted in the coding sequence of the nucleic acid;

(e) a "frameshift mutation", resulting in the nucleic acid sequence being translated in a different frame downstream of the mutation. A frameshift mutation can have various causes, such as the insertion, deletion or duplication of one or more nucleotides.

As already mentioned, it is desired that the mutation(s) in the endogenous gene preferably result in a mutant protein comprising significantly reduced or no biological activity in vivo or in the production of no protein. Basically, any mutation which results in a protein comprising at least one amino acid insertion, deletion and/or substitution relative to the wild type protein can lead to significantly reduced or no biological activity. It is, however, understood that mutations in certain parts of the protein are more likely to result in a reduced function of the mutant APH6 protein, such as mutations leading to truncated proteins, whereby significant portions of the functional domains are lacking.

The term "disruption" or "disrupted" also encompasses that the disrupted gene or one of its products can be functionally inhibited or inactivated such that a gene is either not expressed or is incapable of efficiently expressing a full-length and/or fully functional gene product. Functional inhibition or inactivation can result from a structural disruption and/or interruption of expression at either level of transcription or translation. Functional inhibition or inactivation can also be achieved e.g. by methods such as antisense polynucleotide gene suppression, double stranded RNA induced gene silencing, ribozyme techniques, and the like as specified in detail further below. The inhibition of expression and/or activity can be the result of, e.g. antisense constructs, sense constructs, RNA silencing constructs, RNA interference, genomic disruptions (e.g. transposons, tilling, homologous recombination, etc.), and/or the like. The inhibition of expression and/or activity can be measured by determining the presence and/or amount of transcript (e.g. by Northern blotting or RT-PCR techniques) and/or by determining the presence and/or amount of full length or truncated polypeptide encoded by said gene (e.g. by ELISA or Western blotting) and/or by determining presence and/or amount of protein activity of the product of the disrupted gene.

The term "disruption" or "disrupted" as used herein is to be understood that a disruption also encompasses a disruption which is effective only in a part of a plant, in a particular cell type or tissue like e.g. the reproductive meristem or the shoot apex. A disruption may be achieved by interacting with or affecting within a coding region, within a non-coding region and/or within a regulatory region like e.g. a promoter region of a particular gene. A disruption in the sense of the present invention preferably results in complete or partial loss-of-function of the disrupted gene and/or its product.

At least one of the disruptions of the method of the invention or of the non-naturally occurring plant of the invention can be produced by introducing at least one polynucleotide sequence comprising a nucleic acid sequence which has at least about 90%, at least about 95%, at least about 99%, about 99.5% or more sequence identity to SEQ ID No. 2, 3, 4, 13, 14 or a subsequence thereof, or a complement thereof, into the genome of a plant cell, such that the at least one polynucleotide sequence is linked to a promoter in a sense or antisense orientation. In another embodiment, the disruption is introduced into the genome of a plant cell by introducing at least one polynucleotide sequence configured for RNA silencing or interference.

One, more than one or all disruptions in at least one of the endogenous genes may comprise insertion of one or more transposons. A "transposable element" (TE) or "transposable genetic element" is a DNA sequence that can move from one location to another in a cell. Movement of a transposable element can occur from episome to episome, from episome to chromosome, from chromosome to chromosome, or from chromosome to episome. Transposable elements are characterized by the presence of inverted repeat sequences at their termini. Mobilization is mediated enzymatically by a "transposase". Structurally, a transposable element is categorized as a "transposon" (TN) or an "insertion sequence element" (IS element) based on the presence or absence, respectively, of genetic sequences in addition to those necessary for mobilization of the element. A mini-transposon or mini-IS element typically lacks sequences encoding a transposase.

In yet another embodiment, one, more than one or all disruptions can comprise one or more point mutations in at least one of the endogenous genes.

One, more than one or all disruptions in at least one of the endogenous genes can be homozygous disruptions. Alternatively, one, more than one or all disruptions in at least one of the endogenous genes can be a heterozygous disruption. In certain embodiments, the disruptions in at least one of the endogenous genes can include homozygous disruptions, heterozygous disruptions or a combination of homozygous disruptions and heterozygous disruptions.

The disruption may be introduced by way of introduction of an expression cassette into the genome of the plant. An "expression cassette" is a nucleic acid construct, e.g. a vector, such as a plasmid, a viral vector, etc., capable of producing transcripts and, potentially, polypeptides encoded by a polynucleotide sequence. An expression vector is capable of producing transcripts in an exogenous cell, e.g. a bacterial cell, or a plant cell, in vivo or in vitro, e.g. a cultured plant protoplast. Expression of a product can be either constitutive or inducible depending, e.g. on the promoter selected. Antisense, sense or RNA interference or silencing configurations that are not or cannot be translated are expressly included by this definition. In the context of an expression vector, a promoter is said to be "operably linked" or "functionally linked" to a polynucleotide sequence if it is capable of regulating expression of the associated polynucleotide sequence. The term also applies to alternative exogenous gene constructs, such as expressed or integrated transgenes. Similarly, the term operably or functionally linked applies equally to alternative or additional transcriptional regulatory sequences such as enhancers, associated with a polynucleotide sequence.

The term "vector" refers to the means by which a nucleic acid can be propagated and/or transferred between organisms, cells, or cellular components. Vectors include plasmids, viruses, bacteriophage, pro-viruses, phagemids, transposons, and artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not autonomously replicating.

A polynucleotide sequence, nucleic acid sequence or gene is said to "encode" a sense or antisense RNA molecule, or RNA silencing or interference molecule or a polypeptide, if the polynucleotide sequence can be transcribed (in spliced or unspliced form) and/or translated into the RNA or polypeptide, or a subsequence thereof. The skilled person is well aware of the degeneracy of the genetic code, allowing for a number of different nucleic acid sequences encoding for the same amino acid sequence or polypeptide and has no difficulties in determining whether a given nucleic acid sequence encodes for a given amino acid sequence or polypeptide.

"Expression of a gene" or "expression of a nucleic acid" means transcription of DNA into RNA (optionally including modification of the RNA, e.g. splicing), translation of RNA into a polypeptide (possibly including subsequent modification of the polypeptide, e.g. posttranslational modification), or both transcription and translation, as indicated by the context.

The method of the invention can further comprise the steps of introducing into the plant genome a disruption of endogenous AHP6 gene, and regenerating a plant having such an altered genome. Said disruption may be stably introduced into the genome of the plant in order to generate a non-naturally occurring plant. A disruption is considered stably introduced into the genome of a plant, if said disruption is copied and seggregated during cell division and is passed on to the progeny of said plant or plant cell.

The method of the invention may further comprise the step of introducing into the plant genome the disruption of at least one endogenous CKX gene, e.g. of at least two different endogenous CKX genes.

As used herein the term "CKX gene" or "cytokininoxidase/dehydrogenase gene" refers to a gene encoding for a CKX protein with cytokininoxidase/dehydrogenase activity. A CKX protein, also referred to as cytokininoxidase/dehydrogenase, is an enzyme that catalyzes the chemical reaction:

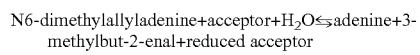

N6-dimethylallyladenine+acceptor+$H_2O$⇌adenine+3-methylbut-2-enal+reduced acceptor The three substrates of this enzyme are N6-dimethylallyladenine, acceptor, and $H_2O$, whereas its three products are adenine, 3-methylbut-2-enal, and reduced acceptor. The term "cytokininoxidase/dehydrogenase activity" encompasses the activity of a given polypeptide to catalyse an oxidoreductase reaction with at least one of the cytokinins as substrate. The skilled person is well aware of means and methods to determine whether a given polypeptide has cytokininoxidase/dehydrogenase activity or not and to determine the level of cytokininoxidase/dehydrogenase activity of a particular polypeptide or probe in absolute values and/or relative to another polypeptide or probe. There is ample guidance in the literature how a given polypeptide can be tested for such an activity, see e.g. EC 1.5.99.12. The term "cytokinin oxidase/dehydrogenase activity" may encompass the activity of a given polypeptide to catalyse an oxidoreductase reaction with at least one of the cytokinins as substrate with an activity of not less than 30% of the activity of AtCKX3 (CKX3 with SEQ ID No. 7), or of not less than 50% of the activity of AtCKX3.

The at least one CKX gene can be:
an endogenous CKX1 gene encoding for a CKX protein comprising an amino acid sequence being identical to or having at least 90% identity with SEQ ID No. 5 or an orthologue thereof;
an endogenous CKX2 gene encoding for a CKX protein comprising an amino acid sequence being identical to or having at least 90% identity with SEQ ID No. 6 or an orthologue thereof;
an endogenous CKX3 gene encoding for a CKX protein comprising an amino acid sequence being identical to or having at least 90% identity with SEQ ID No. 7 or an orthologue thereof;
an endogenous CKX4 gene encoding for a CKX protein comprising an amino acid sequence being identical to or having at least 90% identity with SEQ ID No. 8 or an orthologue thereof;
an endogenous CKX5 gene encoding for a CKX protein comprising an amino acid sequence being identical to or having at least 90% identity with SEQ ID No. 9 or an orthologue thereof;
an endogenous CKX6 gene encoding for a CKX protein comprising an amino acid sequence being identical to or having at least 90% identity with SEQ ID No. 10 or an orthologue thereof; or
an endogenous CKX7 gene encoding for a CKX protein comprising an amino acid sequence being identical to or having at least 90% identity with SEQ ID No. 11 or an orthologue thereof.

In the method of the invention there can be at least two endogenous CKX genes disrupted in addition to disruption of endogenous AHP6 gene. In particular the two endogenous CKX gene to be disrupted are an endogenous CKX3 gene encoding for a CKX protein comprising an amino acid sequence being identical to or having at least 90% identity with SEQ ID No. 7 or an orthologue thereof and an endogenous CKX5 gene encoding for a CKX protein comprising an amino acid sequence being identical to or having at least 90% identity with SEQ ID No. 9 or an orthologue thereof are disrupted.

It has been shown that combination of AHP6 gene disruption with disruption of CKX genes leads to an even more pronounced effect on seed yield.

The method of the invention can be used to achieve an increase in number of siliques per plant and, thereby, an increase in seed yield in a plant and the progeny derived therefrom.

The method of the invention can also be used to produce a non-naturally occurring plant with an increase in number of siliques per plant and, thereby, an increase in seed yield in a plant and the progeny derived therefrom.

The present invention is also directed to a non-naturally occurring plant comprising a disruption in an endogenous AHP6 gene and at least one endogenous CKX gene. E.g. the endogenous AHP6 gene comprises or consists of:
(a) a nucleic acid encoding an AHP6 protein comprising the amino acid sequence of SEQ ID No. 1, 12 or an orthologue thereof;
(b) a nucleic acid encoding an AHP6 protein comprising an amino acid sequence having a sequence identity of at least 70%, at least 80%, at least 90% or at least 95% when compared to the entire amino acid sequence of SEQ ID No. 1 or 12;
(c) a nucleic acid comprising the nucleic acid sequence of SEQ ID No. 2, 3, 4, 13 or 14;
(d) a nucleic acid comprising a nucleic acid sequence having a sequence identity of at least 90% through the entire nucleic acid sequence of SEQ ID No. 2, 3, 4, 13 or 14; or
(e) a nucleic acid hybridizing under stringent conditions to one of the nucleic acid sequences defined under (a), (b), (c) and/or (d).

In the non-naturally occurring plant of the invention the at least one endogenous disrupted CKX gene can be:
an endogenous CKX1 gene encoding for a CKX protein comprising an amino acid sequence being identical to or having at least 90% identity with SEQ ID No. 5 or an orthologue thereof;
an endogenous CKX2 gene encoding for a CKX protein comprising an amino acid sequence being identical to or having at least 90% identity with SEQ ID No. 6 or an orthologue thereof;
an endogenous CKX3 gene encoding for a CKX protein comprising an amino acid sequence being identical to or having at least 90% identity with SEQ ID No. 7 or an orthologue thereof;
an endogenous CKX4 gene encoding for a CKX protein comprising an amino acid sequence being identical to or having at least 90% identity with SEQ ID No. 8 or an orthologue thereof;
an endogenous CKX5 gene encoding for a CKX protein comprising an amino acid sequence being identical to or having at least 90% identity with SEQ ID No. 9 or an orthologue thereof;
an endogenous CKX6 gene encoding for a CKX protein comprising an amino acid sequence being identical to or having at least 90% identity with SEQ ID No. 10 or an orthologue thereof; or
an endogenous CKX7 gene encoding for a CKX protein comprising an amino acid sequence being identical to or having at least 90% identity with SEQ ID No. 11 or an orthologue thereof.

The endogenous CKX genes being disrupted in the non-naturally occurring plant of the invention may be
an endogenous CKX3 gene encoding for a CKX protein comprising an amino acid sequence being identical to or having at least 90% identity with SEQ ID No. 7 or an orthologue thereof; and
an endogenous CKX5 gene encoding for a CKX protein comprising an amino acid sequence being identical to or having at least 90% identity with SEQ ID No. 9 or an orthologue thereof.

The non-naturally occurring plant of the invention can be produced by conventional means like e.g. transformation. The transformation of plant cells and protoplasts can be carried out in essentially any of the various ways known to those skilled in the art of plant molecular biology, including, but not limited to, the methods described herein. See, in general, Methods in Enzymology, Vol. 153 (Recombinant DNA Part D) Wu and Grossman (eds.) 1987, Academic Press. As used herein, the term "transformation" means alteration of the genotype of a host plant or plant cell by the introduction of a nucleic acid sequence, e.g. a "heterologous", "exogenous" or "foreign" nucleic acid sequence. The heterologous nucleic acid sequence need not necessarily originate from a different source but it will, at some point, have been external to the cell into which is introduced.

In the method of the invention and in the non-naturally occurring plant of the invention, the disruption of the endogenous gene can be facilitated by a number of different known techniques.

One, more than one or all of the disruptions in at least one of the endogenous genes can be facilitated by introducing into the genome and expressing in a plant cell or a plant a transgenic polynucleotide sequence, e.g. in antisense or sense configurations, or RNA silencing or interference configurations, etc, wherein the transgenic polynucleotide sequence comprises a nucleic acid sequence being or being complementary to one of the endogenous genes to be disrupted. In addition, said polynucleotide sequence may comprise a promoter, thereby inhibiting expression and/or activity of at least the disrupted endogenous gene compared to a corresponding control plant cell or plant lacking such disruptions (e.g. its non-transgenic parent or a non-transgenic plant of the same species). The transgenic polynucleotide sequence can be introduced by techniques including, but not limited to, e.g. electroporation, micro-projectile bombardment, *Agrobacterium*-mediated transfer, or other available methods. In certain aspects of the invention, the polynucleotide is linked to the promoter in a sense orientation or in an antisense orientation or is configured for RNA silencing or interference.

The disruption of one or more of the endogenous genes can be facilitated by the application of homology-dependent gene silencing, a technique already well described in the literature.

Alternatively, another approach to gene silencing can be with the use of antisense technology. Use of antisense nucleic acids is well known in the art. An antisense nucleic acid has a region of complementarity to a target nucleic acid, e.g. a particular genomic gene sequence, an mRNA, or cDNA. The antisense nucleic acid can be RNA, DNA or any other appropriate molecule. A duplex can form between the antisense sequence and its complementary sense sequence, resulting in inactivation of the gene. The antisense nucleic acid can inhibit gene expression by forming a duplex with an RNA transcribed from the gene, by forming a triplex with duplex DNA, etc. An antisense nucleic acid can be produced and tested by a number of well-established techniques.

Catalytic RNA molecules or ribozymes can also be used to inhibit expression of particular selected genes. It is possible to design ribozymes that specifically pair with virtually any desired target RNA and cleave the phosphodiester backbone at a specific location, thereby functionally inactivating the target RNA. In carrying out this cleavage, the ribozyme is not itself altered, and is thus capable of recycling and cleaving other molecules. The inclusion of ribozyme sequences within antisense RNAs confers RNA-cleaving activity upon them, thereby increasing the activity of the constructs. A number of classes of ribozymes have been identified. For example, one class of ribozymes is derived from a number of small circular RNAs that are capable of self-cleavage and replication in plants. The RNAs can replicate either alone (viroid RNAs) or with a helper virus (satellite RNAs). Examples of RNAs include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes has been described. See, e.g., Haseloff et al. (1988) Nature, 334: 585-591.

Another method to inactivate a particular selected gene by inhibiting expression is by sense suppression. Introduction of expression cassettes in which a nucleic acid is configured in the sense orientation with respect to the promoter has been shown to be an effective means by which to block the transcription of a desired target gene. See, e.g., U.S. Pat. Nos. 5,034,323, 5,231,020 and 5,283,184.

A disruption of the invention can also be produced by using RNA silencing or interference (RNAi), which can also be termed post-transcriptional gene silencing (PTGS) or co-suppression. In the context of this invention, "RNA silencing" (also called RNAi or RNA-mediated interference) refers to any mechanism through which the presence of a single-stranded or, typically, a double-stranded RNA in a cell results in inhibition of expression of a target gene comprising a sequence identical or nearly identical to that of the RNA, including, but not limited to, RNA interference, repression of translation of a target mRNA transcribed from the target gene without alteration of the mRNA's stability, and transcriptional silencing (e.g. histone acetylation and heterochromatin formation leading to inhibition of transcription of the target mRNA). In "RNA interference" the presence of the single-stranded or double-stranded RNA in the cell leads to endonucleolytic cleavage and then degradation of the target mRNA.

In one embodiment, a transgene (e.g. a sequence and/or subsequence of a gene or coding sequence of interest) is introduced into a plant cell to disrupt one or more genes by RNA silencing or interference (RNAi). For example, a sequence or subsequence (the transgene) includes a small subsequence, e.g. about 21-25 bases in length, a larger subsequence, e.g. about 25-100 or about 100-2000 (or about 200-1500, about 250-1000, etc.) bases in length, and/or the entire coding sequence or gene selected from or being complementary to the endogenous gene to be disrupted. Such a transgene can include a region in the sequence or subsequence that is about 21-25 bases in length with at least 80%, at least 90%, or at least 99% identity to a subsequence of one of the nucleic acid sequences with the SEQ ID No. 2, 3. 4, 13 or 14.

Use of RNAi for inhibiting gene expression in a number of cell types (including, e.g. plant cells) and organisms, e.g. by expression of a hairpin (stem-loop) RNA or of the two strands of an interfering RNA, for example, is well described in the literature, as are methods for determining appropriate interfering RNA (s) to target a desired gene, and for generating such interfering RNAs. For example, RNA interference is described e.g. in US patent application publications 20020173478, 20020162126, and 20020182223.

The polynucleotide sequence(s) or subsequence(s) to be expressed to induce RNAi can be expressed, e.g., under control of a constitutive promoter, an inducible promoter, or a tissue specific promoter. Expression from a tissue-specific promoter can be advantageous in certain embodiments. A "promoter", as used herein, includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells, such as *Agrobacterium* or *Rhizobium*. Examples of promoters under developmental control include promoters that preferentially initiate transcription in certain tissues, such as leaves, roots, or seeds or spatially in regions such as endosperm, embryo, or meristematic regions. Such promoters are referred to as "tissue-preferred" or "tissue-specific". A temporally regulated promoter drives expression at particular times, such as between 0-25 days after pollination. A "cell-type-preferred" promoter primarily drives expression in certain cell types in one or more organs, for example, vascular cells in roots or leaves. An "inducible" promoter is a promoter that is under environmental control and may be inducible or de-repressible. Examples of environmental conditions that may effect transcription by inducible promoters include anaerobic conditions or the presence of light. Tissue-specific, cell-typespecific, and inducible promoters constitute the class of "non-constitutive" promoters. A "constitutive" promoter is a promoter that is active under most environmental conditions and in all or nearly all tissues, at all or nearly all stages of development.

One, more than one or all disruptions in at least one of the above-mentioned endogenous genes can be introduced by, e.g. transposon-based gene inactivation. The one or more mutations in the gene sequence can comprise one or more transposon insertions and the disruptions inhibit expression and/or activity of at least the disrupted endogenous gene compared to a corresponding control plant cell or plant lacking such disruptions. For example, the one or more mutations comprise a homozygous disruption in one or more genes mentioned above or the one or more mutations comprise a heterozygous disruption in one or more genes mentioned above or a combination of both homozygous disruptions and heterozygous disruptions.

Transposons were first identified in maize by Barbara McClintock in the late 1940s. The Mutator family of transposable elements, e.g. Robertson's Mutator (Mu) transposable elements, are typically used in plant gene mutagenesis, because they are present in high copy number (10-100) and insert preferentially within and around genes.

Transposable elements can be categorized into two broad classes based on their mode of transposition. These are designated Class I and Class II; both have applications as mutagens and as delivery vectors. Class I transposable elements transpose by an RNA intermediate and use reverse transcriptases, i.e. they are retroelements. There are at least three types of Class I transposable elements, e.g. retrotransposons, retroposons, SINE-like elements. Retrotransposons typically contain LTRs, and genes encoding viral coat proteins (gag) and reverse transcriptase, RnaseH, integrase and polymerase (pol) genes. Numerous retrotransposons have been described in plant species. Such retrotransposons mobilize and translocate via a RNA intermediate in a reaction catalyzed by reverse transcriptase and RNase H encoded by the transposon. Examples fall into the Ty1-copia and Ty3-gypsy groups as well as into the SINE-like and LINE-like classifications. A more detailed discussion can be found in Kumar and Bennetzen (1999) Plant Retrotransposons in Annual Review of Genetics 33: 479.

In addition, DNA transposable elements such as Ac, Taml and En/Spm are also found in a wide variety of plant species, and can be utilized in the invention.

Transposons (and IS elements) are common tools for introducing mutations in plant cells. These mobile genetic elements are delivered to cells, e.g. through a sexual cross, transposition is selected for and the resulting insertion mutants are screened, e.g. for a phenotype of interest. The disrupted genes can then be introduced into other plants by crossing the isolated, non-naturally occurring or transgenic plants with a non-disrupted plant, e.g. by a sexual cross. Any of a number of standard breeding techniques can be used, depending upon the species to be crossed. The location of a TN within a genome of an isolated, non-naturally occurring or transgenic plant can be determined by known methods, e.g. sequencing of flanking regions. For example, a PCR reaction from the plant can be used to amplify the sequence, which can then be diagnostically sequenced to confirm its origin. Optionally, the insertion mutants are screened for a desired phenotype, such as the inhibition of expression or activity of a gene of interest compared to a control plant.

TILLING can also be used to introduce and identify a disruption of the present invention. TILLING is Targeting Induced Local Lesions In Genomes. See, e.g., McCallum et al., (2000), "Targeting Induced Local Lesions In Genomes (TILLING) for Plant Functional Genomics" Plant Physiology 123: 439-442; McCallum et al., (2000), "Targeted screening for induced mutations" Nature Biotechnology 18: 455-457; and, Colbert et al., (2001), "High-Throughput Screening for Induced Point Mutations" Plant Physiology 126: 480-484.

TILLING combines high density point mutations with rapid sensitive detection of the mutations. Typically, ethyl methanesulfonate (EMS) is used to mutagenize plant seed. EMS alkylates guanine, which typically leads to mispairing. For example, seeds are soaked in an about 10-20 mM solution of EMS for about 10 to 20 hours; the seeds are washed and then sown. The plants of this generation are known as M1. M1 plants are then self-fertilized. Mutations that are present in cells that form the reproductive tissues are inherited by the next generation (M2). Typically, M2 plants are screened for mutation in the desired gene and/or for specific phenotypes. For example, DNA from M2 plants is pooled and mutations in a gene of interest are detected by detection of heteroduplex formation. Typically, DNA is prepared from each M2 plant and pooled. The desired gene is amplified by PCR. The pooled sample is then denatured and annealed to allow formation of heteroduplexes. If a mutation is present in one of the plants; the PCR products will be of two types: wild-type and mutant. Pools that include the heteroduplexes are identified by separating the PCR reaction, e.g. by Denaturing High Performance Liquid Chromatography (DPHPLC). DPHPLC detects mismatches in heteroduplexes created by melting and annealing of heteroallelic DNA. Chromatography is performed while heating the DNA. Heteroduplexes have lower thermal stability and form melting bubbles resulting in faster movement in the chromatography column. When heteroduplexes are present in addition to the expected homoduplexes, a double peak is seen. As a result, the pools that carry the mutation in a gene of interest are identified. Individual DNA from plants that make up the selected pooled population can then be identified and sequenced. Optionally, the plant possessing a desired mutation in a gene of interest can be crossed with other plants to remove background mutations.

Other mutagenic methods can also be employed to introduce a disruption of the invention. Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, and N-nitroso-N-ethylurea. Alternatively, ionizing radiation from sources such as X-rays or gamma rays can be used.

The plant containing the desired disruption(s) of the invention can be crossed with other plants to introduce the disruptions into another plant. This can be done using standard breeding techniques.

Homologous recombination can also be used to introduce a disruption of the invention. Homologous recombination has been demonstrated in plants. Homologous recombination can be used to induce targeted gene modifications by specifically targeting a gene of interest in vivo. Mutations in selected portions of a selected gene sequence (including 5' upstream, 3' downstream, and intragenic regions) are made in vitro and introduced into the desired plant using standard techniques. The mutated gene will interact with the target wild-type gene in such a way that homologous recombination and targeted replacement of the wild-type gene will occur in transgenic plants.

The non-naturally occurring plants of the invention, which can be consumed by humans and animals, may also be used, for example directly or after preparation known per se, as foodstuffs or feedstuffs.

The invention further relates to the use of the above-described non-naturally occurring plants of the invention and of the cells, cell cultures, parts, such as, for example, roots, leaves, and non-naturally occurring propagation material such as seeds, tubers, beets/swollen tap roots or fruits derived therefrom for the production of food- or feedstuffs, pharmaceuticals or fine chemicals.

In the following the present invention is further described by way of examples.

BRIEF DESCRIPTION OF THE DRAWINGS

Figures

DETAILED DESCRIPTION OF THE PRESENTLY PREFERRED EMBODIMENTS

Methods

Plant Material and Growth Conditions

The Columbia (Col-0) ecotype of *Arabidopsis thaliana* was used as the wild type. The T-DNA insertion mutants ckx2-S1 (SALK_068485), ckx3-S1 (SALK_050938), ckx4-S1 (SALK_055204), ckx5-S1 (SALK_064309), and ckx6-S1 (SALK_070071) were from the Salk Institute Genomic Analysis Laboratory (Alonso et al., (2003) *Science* 301, 653-657), the transposon insertion mutant ckx4-Z was from the ZIGIA transposon collection (Baumann E, Lewald J, Saedler H, Schulz B, Wsman E (1998) Successful PCR-based reverse genetic screens using an En-1-mutagenised *Arabidopsis thaliana* population generated via single-seed descent. Theoretical and Applied Genetics 97: 729-734), ckx5-G2 (Line ID 332B10) and ckx7-G1 (Line ID 363C02) were from the GABI-KAT collection (Rosso, M. G., Li, Y., Strizhov, N., Reiss, B., Dekker, K., and Weisshaar, B. (2003) *Plant Mol. Biol.* 53, 247-259) and ckx7-T1 (SAIL_515_A07) was from the Torrey Mesa Research Institute (now Syngenta). The ahp6-1 allele was identified and isolated in a suppressor screen for the determinate root growth associated with the wol mutation of the cytokinin receptor CRE1/AHK4 (Mähönen, A. P., Bonke, M., Kauppinen, L., Riikonen, M., Benfey, P. N., and Helariutta, Y. (2000). A novel two-component hybrid molecule regulates vascular morphogenesis of the *Arabidopsis* root. *Genes Dev.* 14, 2938-2943; and Mähönen, A. P., Bishopp, A., Higuchi, M., Nieminen, K. M., Kinoshita, K., Tormakangas, K., Ikeda, Y., Oka, A., Kakimoto, T., and Helariutta, Y. (2006). Cytokinin signaling and its inhibitor AHP6 regulate cell fate during vascular development. *Science* 311, 94-98.). The ahp6-3 allele is a T-DNA insertion representing likely a null allele and suppressing the wol phenotype in a similar manner as ahp6-1 (Mähönen et al., 2006). Multiple mutants were obtained by genetic crossing. Plants were grown in the greenhouse on soil at 22° C. under long-day conditions (16 h light/8 h dark). For seed yield measurement plants were grown in growth chambers (Percival AR-66L) on soil at 24° C. in ~100 μE and 65% humidity under long-day conditions.

Determination of Yield Parameters

Figure 1:
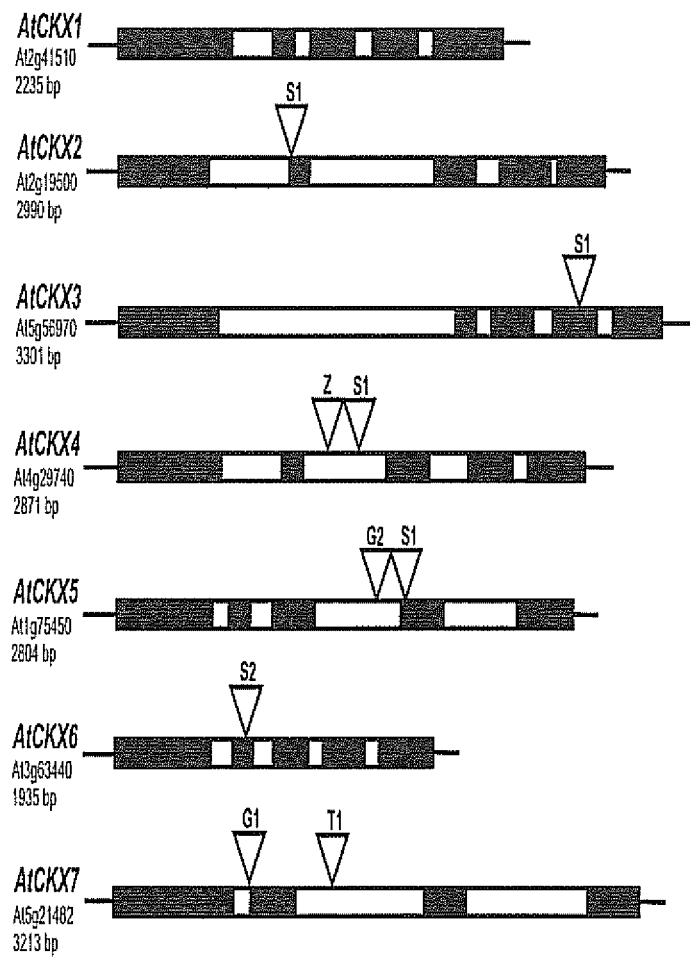
FIG. 1: shows positions of T-DNA and transposon insertions in the ckx mutants. The insertional mutants were identified by PCR screening, and the site of insertion determined by DNA sequencing of the border fragment. Black boxes represent exons, white boxes represent introns, and triangles indicate T-DNA insertions. G, GABI-KAT T-DNA-collection; S, Salk T-DNA-collection; T, Torrey Mesa T-DNA-collection; Z, ZIGIA transposon collection.
Figure 2:
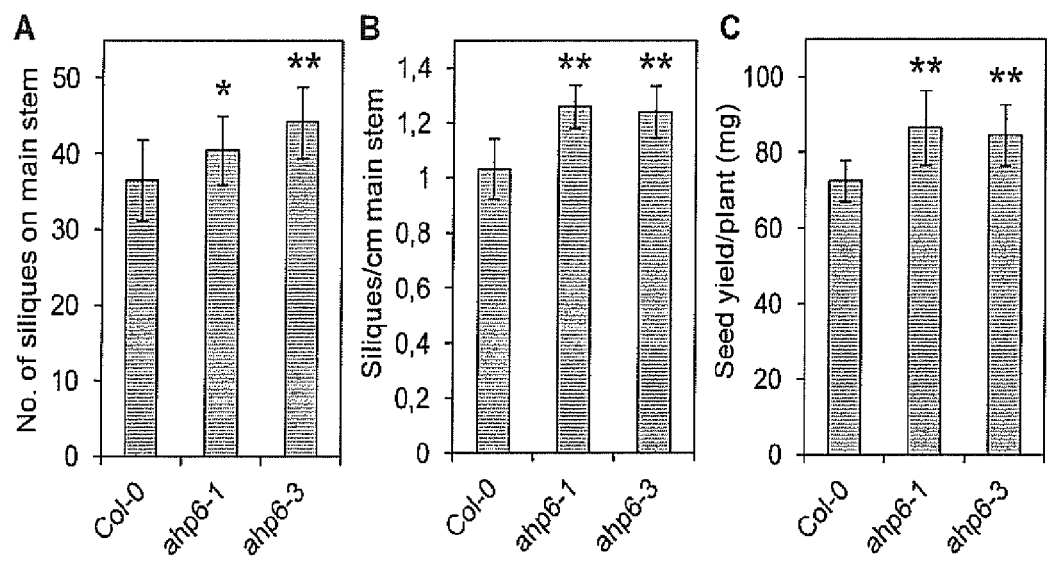
FIG. 2: shows the reproductive development of ahp6-1 and ahp6-3 in comparison to *Arabidopsis* wild type (Col-0): (A.) The number of siliques on the main inflorescence stem of one individual plant. (B.) The density of siliques on the main inflorescence stem. (C.) Total seed yield of wild type and ahp6 mutant plants. Plants were grown in the greenhouse under long day conditions. Data represent mean values±SD (n=20). Student's t test was used to compare values to the wild type. *, P<0.01; **, P<0.0001.

The number of siliques on the main stem was determined after termination of flowering. The number of siliques on the main stem is a well reckognized indicator for seed yield. An increase in number of siliques on the main stem usually indicates an increase in total seed yield per plant (as can be taken from FIGS. 2 A and 2 C). For direct analysis of seed yield, plants were put into paper bags after termination of flowering, and kept dry for additional three weeks before the total seed weight was determined.

EXAMPLES

We compared the reproductive development of ahp6 mutant plants to wild type control plants. Flowers in *Arabidopsis* are continuously formed by the indeterminate inflorescence meristem. Both ahp6 mutants formed larger inflorescences which consisted of significantly more flowers than in the wild type. The larger number of flowers formed by the ahp6 inflorescence meristems led to an increased number of siliques compared to the wild type (FIG. 2A). The number of siliques on the main stem after formation of the last flower was compared. The ahp6-1 and ahp6-3 mutants produced 11 and 21% more siliques than wild-type plants, respectively (FIG. 2A). Moreover, the density of siliques on ahp inflorescence stems was increased. The number of siliques per length unit of the inflorescence stem was increased by 22 and 20% in ahp6-1 and ahp6-3 mutants, respectively, in comparison to wild-type plants (FIG. 2B). To test whether the increased flower and silique formation would influence the seed yield of the mutant plants, we harvested all seeds from individual plants after the termination of flowering and determinated the seed weight. The total seed yield of ahp6-1 and ahp6-3 mutants increased by 19.5 and 16.7% compared to the wild type, respectively (FIG. 2C).

Figure 3:
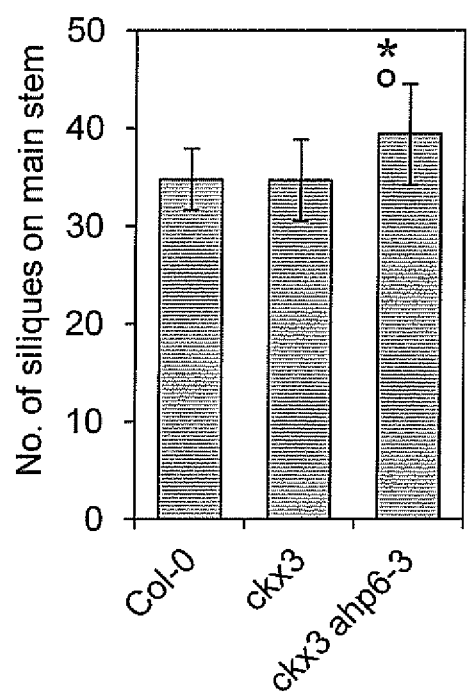
FIG. 3 shows the reproductive development of ckx3 and ckx3 ahp6-3 double mutant in comparison to *Arabidopsis* wild type: The chart represents the number of siliques on the main inflorescence stem. Data represent mean values±SD (n=20). Student's t test was used for statistical comparison. * and °, P<0.01; *=compared to WT, °=compared to ckx3.
Figure 4:
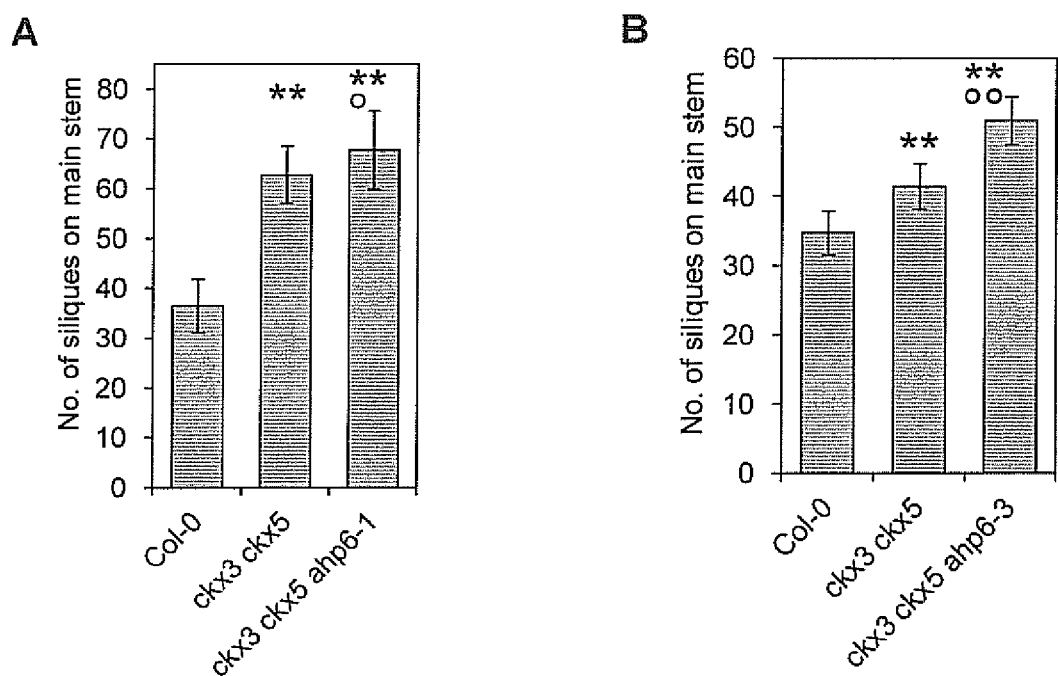
FIG. 4 shows the reproductive development of ckx3 ckx5 double mutant and ckx3 ckx5 ahp6 triple mutant in comparison to *Arabidopsis* wild type: in (A) the chart represents the number of siliques on the main inflorescence stem for ckx3 ckx5 ahp6-1 triple mutant and controls. Data represent mean values±SD (n=20). Student's t test was used for statistical comparison. °, P<0.05; **, P<0.0001; *=compared to WT, °=compared to ckx3 ckx5; whereas in (B) the chart represents the number of siliques on the main inflorescence stem for ckx3 ckx5 ahp6-3 triple mutant and controls. Data represent mean values±SD (n=20). Student's t test was used for statistical comparison. * and °, P<0.01; ** and °°, P<0.0001; *=compared to WT, °=compared to ckx3 ckx5.

To analyze the effect of ahp6 mutation on the reproductive development in plants with an already increased cytokinin status, achieved by mutation of one or more CKX genes, we introduced the ahp6 mutation into ckx3 and ckx3 ckx5 mutant background by genetic crossing and analyzed the resulting hybrid plants. The number of flowers and developed siliques on the main stem of the ckx3 mutant plant was similar to the wild-type control (FIG. 3). However, the combination of ckx3 and ahp6 mutations led to an increase in inflorescence size and to an about 14% increase in silique formation compared to wild-type and ckx3 plants (FIG. 3). Similarly, ahp6 mutation enhanced the reproductive activity of plants carrying mutations in multiple CKX genes. For example, ckx3 ckx5 double mutant plants develop more siliques on the main stem as compared to wild-type control (FIGS. 4A and 4B). However, in ckx3 ckx5 ahp6 triple mutant plants the number of siliques was further increased significantly in comparison to ckx3 ckx5 double mutant plants, resulting in total in an even more pronounced increase of siliques on main stem in ckx3 ckx5 ahp6 triple mutant plants in comparison to the wild type (FIG. 4A for ahp6-1 and FIG. 4B for ahp6-3).

The invention claimed is:

1. A method for increasing seed yield in a plant, the method comprising disruption of
   an endogenous AHP6 gene in cells of the plant, wherein said disruption inhibits expression and/or activity of a product of said endogenous AHP6 gene compared to a corresponding control plant lacking such a disruption, wherein the endogenous AHP6 gene encodes for an AHP6 protein which is a member of the structural family of histidine phosphotransfer kinase/transferase proteins; lacks a histidine at a position corresponding to the position Asn83 of SEQ ID No. 1; and exhibits essentially the same function as AHP6 protein with SEQ ID No. 1 or 12; and
   wherein the method further comprises the step of introducing into the plant genome the disruption of at least one endogenous CKX gene, wherein the at least one CKX gene is selected from:
   an endogenous CKX3 gene encoding for a CKX protein comprising an amino acid sequence being identical to or having at least 90% identity with SEQ ID No. 7; and
   an endogenous CKX5 gene encoding for a CKX protein comprising an amino acid sequence being identical to or having at least 90% identity with SEQ ID No. 9.

2. The method of claim 1, the method comprising the steps of:
   introducing into the plant genome a disruption of endogenous AHP6 gene, and regenerating a plant having such an altered genome.

3. The method of claim 2, wherein the disruption is stably introduced into the plant genome.

4. The method of claim 1, wherein the endogenous AHP6 gene comprises or consists of:
   (a) a nucleic acid encoding an AHP6 protein comprising the amino acid sequence of SEQ ID No. 1 or 12;
   (b) a nucleic acid encoding an AHP6 protein comprising an amino acid sequence having a sequence identity of at least 90% through the entire amino acid sequence of SEQ ID No. 1 or 12;
   (c) a nucleic acid comprising the nucleic acid sequence of SEQ ID No. 2, 3, 4, 13 or 14;
   (d) a nucleic acid comprising a nucleic acid sequence having a sequence identity of at least 90% through the entire nucleic acid sequence of SEQ ID No. 2, 3, 4, 13 or 14.

5. The method of claim 1, wherein an endogenous CKX3 gene encoding for a CKX protein comprising an amino acid sequence being identical to or having at least 90% identity with SEQ ID No. 7 and an endogenous CKX5 gene encoding for a CKX protein comprising an amino acid sequence being identical to or having at least 90% identity with SEQ ID No. 9 are disrupted.

6. The method of claim 1, wherein one, more than one or all disruptions are introduced by structural disruption, antisense polynucleotide gene suppression, double stranded RNA induced gene silencing, ribozyme techniques, genomic disruption, tilling and/or homologous recombination.

7. The method of claim 1, wherein one, more than one or all disruptions are homozygous disruptions.

8. A non-naturally occurring plant comprising a disruption in an endogenous AHP6 gene and at least one endogenous CKX gene, wherein the endogenous AHP6 gene comprises or consists of:
- (a) a nucleic acid encoding an AHP6 protein comprising the amino acid sequence of SEQ ID No. 1 or 12;
- (b) a nucleic acid encoding an AHP6 protein comprising an amino acid sequence having a sequence identity of at least 90% through the entire amino acid sequence of SEQ ID No. 1 or 12;
- (c) a nucleic acid comprising the nucleic acid sequence of SEQ ID No. 2, 3, 4, 13 or 14;
- (d) a nucleic acid comprising a nucleic acid sequence having a sequence identity of at least 90% through the entire nucleic acid sequence of SEQ ID No. 2, 3, 4, 13 or 14; and wherein the at least one CKX gene is selected from:

an endogenous CKX3 gene encoding for a CKX protein comprising an amino acid sequence being identical to or having at least 90% identity with SEQ ID No. 7; and an endogenous CKX5 gene encoding for a CKX protein comprising an amino acid sequence being identical to or having at least 90% identity with SEQ ID No. 9.

9. The method of claim 1, wherein the AHP6 protein lacks phosphotransfer activity and acts as inhibitor of cytokinin signaling.

\* \* \* \* \*

SEQUENCE LISTING

<160> NUMBER OF SEQ ID NOS: 14

<210> SEQ ID NO 1
<211> LENGTH: 154
<212> TYPE: PRT
<213> ORGANISM: Arabidopsis thaliana

<400> SEQUENCE: 1

```
Met Leu Gly Leu Gly Val Asp Arg Leu Gln Ala Asp Ile Asn Arg Leu
1               5                   10                  15

Leu Ala Ser Leu Phe His Gln Gly Val Leu Asp Glu Gln Phe Leu Gln
            20                  25                  30

Leu Gln Gln Leu Gln Asp Glu Thr Ser Pro Asn Phe Val Tyr Asp Val
        35                  40                  45

Ile Asn Ile Tyr Phe Asp Glu Ser Glu Lys Leu Leu Arg Asn Leu Arg
    50                  55                  60

Leu Leu Leu Met Asp Arg Glu Phe Ser Asp Tyr Lys Lys Ile Gly Leu
65                  70                  75                  80

His Leu Asn Gln Leu Val Gly Ser Ser Ser Ile Gly Ala Arg Arg
                85                  90                  95

Val Arg Asn Val Cys Val Ala Phe Arg Ser Ala Ser Glu Leu Ser Asn
                100                 105                 110

Arg Pro Gly Cys Leu Arg Gly Leu Glu Val Val Glu His Glu Tyr His
            115                 120                 125

Tyr Leu Lys Asn Met Met His Glu Leu Phe Gln Leu Glu Gln Gln Arg
        130                 135                 140

Ile Leu Ala Ala Gly Val Arg Tyr Pro Met
145                 150
```

<210> SEQ ID NO 2
<211> LENGTH: 835
<212> TYPE: DNA
<213> ORGANISM: Arabidopsis thaliana

<400> SEQUENCE: 2

```
atgttggggt tgggtgtgga ccggcttcaa gccgacatca accggctcct agcctctctt        60
ttccaccagg gagtgctgga cgagcagttc ttgcagcttc agcagcttca agatgagact       120
tcaccaaact ttgtgtatga tgtcattaat atctactttg atgaatccga gaagttactc       180
cgcaacctta gattattgtt gtgagtttct tcctttgtta atgtgttcca tagttgtatg       240
ttgtttggtt ccaaaatgta tacgtatata tatgttatga atgatgacga atgtaaataa       300
ataaatgaac aggatggata gagaattctc ggactataag aaaataggat tacacctgaa       360
tcagctggtg ggaagcagtt caagcattgg tgctcgtagg gttcgtaacg tctgcgttgc       420
ctttcgttct gcttccgagc ttagcaaccg cccagggtac aaattaaacg agctatatat       480
atatatatat atatatatat atatatactt ctttgtatta atatataggt caatatttaa       540
```

```
gtcaatataa tgcttcataa atgtgacgat gcttcaggtg cttgagagga ctggaggtag    600
tagagcatga gtatcattac ctcaagaaca tgatgcatga actcttccag gtacttactt    660
gttttgttaa tatattactc acattcacac aaacagaagg caaaacgtg agctaaatat     720 acacatatat attgatagta atatatgtta acaattatgt gggatttaat attttgagtg    780
gttgcagctg gagcagcaga gaatattagc tgcaggagtc agatatccaa tgtaa         835
```

<210> SEQ ID NO 3
<211> LENGTH: 465
<212> TYPE: DNA
<213> ORGANISM: Arabidopsis thaliana

<400> SEQUENCE: 3

```
atgttggggt tgggtgtgga ccggcttcaa gccgacatca accggctcct agcctctctt    60
ttccaccagg gagtgctgga cgagcagttc ttgcagcttc agcagcttca agatgagact    120
tcaccaaact ttgtgtatga tgtcattaat atctactttg atgaatccga gaagttactc    180
cgcaacctta gattattgtt gatggataga gaattctcgg actataagaa aataggatta    240
cacctgaatc agctggtggg aagcagttca agcattggtg ctcgtagggt tcgtaacgtc    300
tgcgttgcct ttcgttctgc ttccgagctt agcaaccgcc cagggtgctt gagaggactg    360
gaggtagtag agcatgagta tcattacctc aagaacatga tgcatgaact cttccagctg    420
gagcagcaga gaatattagc tgcaggagtc agatatccaa tgtaa                    465
```

<210> SEQ ID NO 4
<211> LENGTH: 640
<212> TYPE: DNA
<213> ORGANISM: Arabidopsis thaliana

<400> SEQUENCE: 4

```
gaagcaagac ctgttcacat tagtaaaaac aaatatatag aaagaggaaa gattgaagcg    60
gaaaacggga caagacgggt gtgccgttgt ggatgttggg gttgggtgtg gaccggcttc    120
aagccgacat caaccggctc ctagcctctc ttttccacca gggagtgctg gacgagcagt    180
tcttgcagct tcagcagctt caagatgaga cttcaccaaa ctttgtgtat gatgtcatta    240
atatctactt tgatgaatcc gagaagttac tccgcaacct tagattattg ttgatggata    300
gagaattctc ggactataag aaaataggat tacacctgaa tcagctggtg ggaagcagtt    360
caagcattgg tgctcgtagg gttcgtaacg tctgcgttgc cttttcgttct gcttccgagc   420 ttagcaaccg cccagggtgc ttgagaggac tggaggtagt agagcatgag tatcattacc    480
tcaagaacat gatgcatgaa ctcttccagc tggagcagca gagaatatta gctgcaggag    540
tcagatatcc aatgtaaaat tagaattttg tcataaaaat cagagaaaac ctaattagtg    600
tgtgatgata gtgtgttata agctaccgaa gcgaaaccct                          640
```

<210> SEQ ID NO 5
<211> LENGTH: 575
<212> TYPE: PRT
<213> ORGANISM: Arabidopsis thaliana

<400> SEQUENCE: 5

```
Met Gly Leu Thr Ser Ser Leu Arg Phe His Arg Gln Asn Asn Lys Thr
1               5                   10                  15

Phe Leu Gly Ile Phe Met Ile Leu Val Leu Ser Cys Ile Pro Gly Arg
            20                  25                  30
```

```
Thr Asn Leu Cys Ser Asn His Ser Val Ser Thr Pro Lys Glu Leu Pro
         35                  40                  45

Ser Ser Asn Pro Ser Asp Ile Arg Ser Ser Leu Val Ser Leu Asp Leu
 50                  55                  60

Glu Gly Tyr Ile Ser Phe Asp Val His Asn Val Ala Lys Asp Phe
 65                  70                  75                  80

Gly Asn Arg Tyr Gln Leu Pro Pro Leu Ala Ile Leu His Pro Arg Ser
                 85                  90                  95

Val Phe Asp Ile Ser Ser Met Met Lys His Ile Val His Leu Gly Ser
             100                 105                 110

Thr Ser Asn Leu Thr Val Ala Ala Arg Gly His Gly His Ser Leu Gln
         115                 120                 125

Gly Gln Ala Leu Ala His Gln Gly Val Val Ile Lys Met Glu Ser Leu
130                 135                 140

Arg Ser Pro Asp Ile Arg Ile Tyr Lys Gly Lys Gln Pro Tyr Val Asp
145                 150                 155                 160

Val Ser Gly Gly Glu Ile Trp Ile Asn Ile Leu Arg Glu Thr Leu Lys
                 165                 170                 175

Tyr Gly Leu Ser Pro Lys Ser Trp Thr Asp Tyr Leu His Leu Thr Val
             180                 185                 190

Gly Gly Thr Leu Ser Asn Ala Gly Ile Ser Gly Gln Ala Phe Lys His
         195                 200                 205

Gly Pro Gln Ile Asn Asn Val Tyr Gln Leu Glu Ile Val Thr Gly Lys
     210                 215                 220

Gly Glu Val Val Thr Cys Ser Glu Lys Arg Asn Ser Glu Leu Phe Phe
225                 230                 235                 240

Ser Val Leu Gly Gly Leu Gly Gln Phe Gly Ile Ile Thr Arg Ala Arg
                 245                 250                 255

Ile Ser Leu Glu Pro Ala Pro His Met Val Lys Trp Ile Arg Val Leu
             260                 265                 270

Tyr Ser Asp Phe Ser Ala Phe Ser Arg Asp Gln Glu Tyr Leu Ile Ser
         275                 280                 285

Lys Glu Lys Thr Phe Asp Tyr Val Glu Gly Phe Val Ile Ile Asn Arg
290                 295                 300

Thr Asp Leu Leu Asn Asn Trp Arg Ser Ser Phe Ser Pro Asn Asp Ser
305                 310                 315                 320

Thr Gln Ala Ser Arg Phe Lys Ser Asp Gly Lys Thr Leu Tyr Cys Leu
                 325                 330                 335

Glu Val Val Lys Tyr Phe Asn Pro Glu Glu Ala Ser Ser Met Asp Gln
             340                 345                 350

Glu Thr Gly Lys Leu Leu Ser Glu Leu Asn Tyr Ile Pro Ser Thr Leu
         355                 360                 365

Phe Ser Ser Glu Val Pro Tyr Ile Glu Phe Leu Asp Arg Val His Ile
370                 375                 380

Ala Glu Arg Lys Leu Arg Ala Lys Gly Leu Trp Glu Val Pro His Pro
385                 390                 395                 400

Trp Leu Asn Leu Leu Ile Pro Lys Ser Ser Ile Tyr Gln Phe Ala Thr
                 405                 410                 415

Glu Val Phe Asn Asn Ile Leu Thr Ser Asn Asn Gly Pro Ile Leu
             420                 425                 430

Ile Tyr Pro Val Asn Gln Ser Lys Trp Lys Lys His Thr Ser Leu Ile
         435                 440                 445

Thr Pro Asn Glu Asp Ile Phe Tyr Leu Val Ala Phe Leu Pro Ser Ala
```

```
            450                 455                 460
Val Pro Asn Ser Ser Gly Lys Asn Asp Leu Glu Tyr Leu Leu Lys Gln
465                 470                 475                 480

Asn Gln Arg Val Met Asn Phe Cys Ala Ala Ala Asn Leu Asn Val Lys
                485                 490                 495

Gln Tyr Leu Pro His Tyr Glu Thr Gln Lys Glu Trp Lys Ser His Phe
            500                 505                 510

Gly Lys Arg Trp Glu Thr Phe Ala Gln Arg Lys Gln Ala Tyr Asp Pro
        515                 520                 525

Leu Ala Ile Leu Ala Pro Gly Gln Arg Ile Phe Gln Lys Thr Thr Gly
    530                 535                 540

Lys Leu Ser Pro Ile Gln Leu Ala Lys Ser Lys Ala Thr Gly Ser Pro
545                 550                 555                 560

Gln Arg Tyr His Tyr Ala Ser Ile Leu Pro Lys Pro Arg Thr Val
                565                 570                 575

<210> SEQ ID NO 6
<211> LENGTH: 501
<212> TYPE: PRT
<213> ORGANISM: Arabidopsis thaliana

<400> SEQUENCE: 6

Met Ala Asn Leu Arg Leu Met Ile Thr Leu Ile Thr Val Leu Met Ile
1               5                   10                  15

Thr Lys Ser Ser Asn Gly Ile Lys Ile Asp Leu Pro Lys Ser Leu Asn
                20                  25                  30

Leu Thr Leu Ser Thr Asp Pro Ser Ile Ile Ser Ala Ala Ser His Asp
            35                  40                  45

Phe Gly Asn Ile Thr Thr Val Thr Pro Gly Gly Val Ile Cys Pro Ser
        50                  55                  60

Ser Thr Ala Asp Ile Ser Arg Leu Leu Gln Tyr Ala Ala Asn Gly Lys
65                  70                  75                  80

Ser Thr Phe Gln Val Ala Ala Arg Gly Gln Gly His Ser Leu Asn Gly
                85                  90                  95

Gln Ala Ser Val Ser Gly Gly Val Ile Val Asn Met Thr Cys Ile Thr
            100                 105                 110

Asp Val Val Val Ser Lys Asp Lys Lys Tyr Ala Asp Val Ala Ala Gly
        115                 120                 125

Thr Leu Trp Val Asp Val Leu Lys Lys Thr Ala Glu Lys Gly Val Ser
    130                 135                 140

Pro Val Ser Trp Thr Asp Tyr Leu His Ile Thr Val Gly Gly Thr Leu
145                 150                 155                 160

Ser Asn Gly Gly Ile Gly Gly Gln Val Phe Arg Asn Gly Pro Leu Val
                165                 170                 175

Ser Asn Val Leu Glu Leu Asp Val Ile Thr Gly Lys Gly Glu Met Leu
            180                 185                 190

Thr Cys Ser Arg Gln Leu Asn Pro Glu Leu Phe Tyr Gly Val Leu Gly
        195                 200                 205

Gly Leu Gly Gln Phe Gly Ile Ile Thr Arg Ala Arg Ile Val Leu Asp
    210                 215                 220

His Ala Pro Lys Arg Ala Lys Trp Phe Arg Met Leu Tyr Ser Asp Phe
225                 230                 235                 240

Thr Thr Phe Thr Lys Asp Gln Glu Arg Leu Ile Ser Met Ala Asn Asp
                245                 250                 255
```

-continued

```
Ile Gly Val Asp Tyr Leu Glu Gly Gln Ile Phe Leu Ser Asn Gly Val
                260                 265                 270

Val Asp Thr Ser Phe Phe Pro Ser Asp Gln Ser Lys Val Ala Asp
            275                 280                 285

Leu Val Lys Gln His Gly Ile Ile Tyr Val Leu Glu Val Ala Lys Tyr
        290                 295                 300

Tyr Asp Asp Pro Asn Leu Pro Ile Ile Ser Lys Val Ile Asp Thr Leu
305                 310                 315                 320

Thr Lys Thr Leu Ser Tyr Leu Pro Gly Phe Ile Ser Met His Asp Val
                325                 330                 335

Ala Tyr Phe Asp Phe Leu Asn Arg Val His Val Glu Glu Asn Lys Leu
            340                 345                 350

Arg Ser Leu Gly Leu Trp Glu Leu Pro His Pro Trp Leu Asn Leu Tyr
        355                 360                 365

Val Pro Lys Ser Arg Ile Leu Asp Phe His Asn Gly Val Val Lys Asp
    370                 375                 380

Ile Leu Leu Lys Gln Lys Ser Ala Ser Gly Leu Ala Leu Leu Tyr Pro
385                 390                 395                 400

Thr Asn Arg Asn Lys Trp Asp Asn Arg Met Ser Ala Met Ile Pro Glu
                405                 410                 415

Ile Asp Glu Asp Val Ile Tyr Ile Ile Gly Leu Leu Gln Ser Ala Thr
            420                 425                 430

Pro Lys Asp Leu Pro Glu Val Glu Ser Val Asn Glu Lys Ile Ile Arg
        435                 440                 445

Phe Cys Lys Asp Ser Gly Ile Lys Ile Lys Gln Tyr Leu Met His Tyr
    450                 455                 460

Thr Ser Lys Glu Asp Trp Ile Glu His Phe Gly Ser Lys Trp Asp Asp
465                 470                 475                 480

Phe Ser Lys Arg Lys Asp Leu Phe Asp Pro Lys Lys Leu Leu Ser Pro
                485                 490                 495

Gly Gln Asp Ile Phe
            500

<210> SEQ ID NO 7
<211> LENGTH: 523
<212> TYPE: PRT
<213> ORGANISM: Arabidopsis thaliana

<400> SEQUENCE: 7

Met Ala Ser Tyr Asn Leu Arg Ser Gln Val Arg Leu Ile Ala Ile Thr
1               5                   10                  15

Ile Val Ile Ile Ile Thr Leu Ser Thr Pro Ile Thr Thr Asn Thr Ser
            20                  25                  30

Pro Gln Pro Trp Asn Ile Leu His Asn Glu Phe Ala Gly Lys Leu
        35                  40                  45

Thr Ser Ser Ser Ser Val Glu Ser Ala Ala Thr Asp Phe Gly His
    50                  55                  60

Val Thr Lys Ile Phe Pro Ser Ala Val Leu Ile Pro Ser Ser Val Glu
65                  70                  75                  80

Asp Ile Thr Asp Leu Ile Lys Leu Ser Phe Asp Ser Gln Leu Ser Phe
                85                  90                  95

Pro Leu Ala Ala Arg Gly His Gly His Ser Arg Gly Gln Ala Ser
        100                 105                 110

Ala Lys Asp Gly Val Val Val Asn Met Arg Ser Met Val Asn Arg Asp
    115                 120                 125
```

```
Arg Gly Ile Lys Val Ser Arg Thr Cys Leu Tyr Val Asp Val Asp Ala
        130                 135                 140

Ala Trp Leu Trp Ile Glu Val Leu Asn Lys Thr Leu Glu Leu Gly Leu
145                 150                 155                 160

Thr Pro Val Ser Trp Thr Asp Tyr Leu Tyr Leu Thr Val Gly Gly Thr
                165                 170                 175

Leu Ser Asn Gly Gly Ile Ser Gly Gln Thr Phe Arg Tyr Gly Pro Gln
            180                 185                 190

Ile Thr Asn Val Leu Glu Met Asp Val Ile Thr Gly Lys Gly Glu Ile
        195                 200                 205

Ala Thr Cys Ser Lys Asp Met Asn Ser Asp Leu Phe Phe Ala Val Leu
210                 215                 220

Gly Gly Leu Gly Gln Phe Gly Ile Ile Thr Arg Ala Arg Ile Lys Leu
225                 230                 235                 240

Glu Val Ala Pro Lys Arg Ala Lys Trp Leu Arg Phe Leu Tyr Ile Asp
                245                 250                 255

Phe Ser Glu Phe Thr Arg Asp Gln Glu Arg Val Ile Ser Lys Thr Asp
            260                 265                 270

Gly Val Asp Phe Leu Glu Gly Ser Ile Met Val Asp His Gly Pro Pro
        275                 280                 285

Asp Asn Trp Arg Ser Thr Tyr Tyr Pro Pro Ser Asp His Leu Arg Ile
290                 295                 300

Ala Ser Met Val Lys Arg His Arg Val Ile Tyr Cys Leu Glu Val Val
305                 310                 315                 320

Lys Tyr Tyr Asp Glu Thr Ser Gln Tyr Thr Val Asn Glu Glu Met Glu
                325                 330                 335

Glu Leu Ser Asp Ser Leu Asn His Val Arg Gly Phe Met Tyr Glu Lys
            340                 345                 350

Asp Val Thr Tyr Met Asp Phe Leu Asn Arg Val Arg Thr Gly Glu Leu
        355                 360                 365

Asn Leu Lys Ser Lys Gly Gln Trp Asp Val Pro His Pro Trp Leu Asn
370                 375                 380

Leu Phe Val Pro Lys Thr Gln Ile Ser Lys Phe Asp Asp Gly Val Phe
385                 390                 395                 400

Lys Gly Ile Ile Leu Arg Asn Asn Ile Thr Ser Gly Pro Val Leu Val
                405                 410                 415

Tyr Pro Met Asn Arg Asn Lys Trp Asn Asp Arg Met Ser Ala Ala Ile
            420                 425                 430

Pro Glu Glu Asp Val Phe Tyr Ala Val Gly Phe Leu Arg Ser Ala Gly
        435                 440                 445

Phe Asp Asn Trp Glu Ala Phe Asp Gln Glu Asn Met Glu Ile Leu Lys
450                 455                 460

Phe Cys Glu Asp Ala Asn Met Gly Val Ile Gln Tyr Leu Pro Tyr His
465                 470                 475                 480

Ser Ser Gln Glu Gly Trp Val Arg His Phe Gly Pro Arg Trp Asn Ile
                485                 490                 495

Phe Val Glu Arg Lys Tyr Lys Tyr Asp Pro Lys Met Ile Leu Ser Pro
            500                 505                 510

Gly Gln Asn Ile Phe Gln Lys Ile Asn Ser Ser
        515                 520
```

<210> SEQ ID NO 8
<211> LENGTH: 524

<212> TYPE: PRT
<213> ORGANISM: Arabidopsis thaliana

<400> SEQUENCE: 8

```
Met Thr Asn Thr Leu Cys Leu Ser Leu Ile Thr Ile Thr Leu Phe
1               5                   10                  15

Ile Ser Leu Thr Pro Thr Leu Ile Lys Ser Asp Glu Gly Ile Asp Val
            20                  25                  30

Phe Leu Pro Ile Ser Leu Asn Leu Thr Val Leu Thr Asp Pro Phe Ser
            35                  40                  45

Ile Ser Ala Ala Ser His Asp Phe Gly Asn Ile Thr Asp Glu Asn Pro
50                  55                  60

Gly Ala Val Leu Cys Pro Ser Ser Thr Thr Glu Val Ala Arg Leu Leu
65                  70                  75                  80

Arg Phe Ala Asn Gly Gly Phe Ser Tyr Asn Lys Gly Ser Thr Ser Pro
                85                  90                  95

Ala Ser Thr Phe Lys Val Ala Ala Arg Gly Gln Gly His Ser Leu Arg
            100                 105                 110

Gly Gln Ala Ser Ala Pro Gly Gly Val Val Asn Met Thr Cys Leu
            115                 120                 125

Ala Met Ala Ala Lys Pro Ala Ala Val Val Ile Ser Ala Asp Gly Thr
130                 135                 140

Tyr Ala Asp Val Ala Ala Gly Thr Met Trp Val Asp Val Leu Lys Ala
145                 150                 155                 160

Ala Val Asp Arg Gly Val Ser Pro Val Thr Trp Thr Asp Tyr Leu Tyr
                165                 170                 175

Leu Ser Val Gly Gly Thr Leu Ser Asn Ala Gly Ile Gly Gly Gln Thr
            180                 185                 190

Phe Arg His Gly Pro Gln Ile Ser Asn Val His Glu Leu Asp Val Ile
            195                 200                 205

Thr Gly Lys Gly Glu Met Met Thr Cys Ser Pro Lys Leu Asn Pro Glu
210                 215                 220

Leu Phe Tyr Gly Val Leu Gly Gly Leu Gly Gln Phe Gly Ile Ile Thr
225                 230                 235                 240

Arg Ala Arg Ile Ala Leu Asp His Ala Pro Thr Arg Val Lys Trp Ser
                245                 250                 255

Arg Ile Leu Tyr Ser Asp Phe Ser Ala Phe Lys Arg Asp Gln Glu Arg
            260                 265                 270

Leu Ile Ser Met Thr Asn Asp Leu Gly Val Asp Phe Leu Glu Gly Gln
            275                 280                 285

Leu Met Met Ser Asn Gly Phe Val Asp Thr Ser Phe Pro Leu Ser
290                 295                 300

Asp Gln Thr Arg Val Ala Ser Leu Val Asn Asp His Arg Ile Ile Tyr
305                 310                 315                 320

Val Leu Glu Val Ala Lys Tyr Tyr Asp Arg Thr Thr Leu Pro Ile Ile
                325                 330                 335

Asp Gln Val Ile Asp Thr Leu Ser Arg Thr Leu Gly Phe Ala Pro Gly
            340                 345                 350

Phe Met Phe Val Gln Asp Val Pro Tyr Phe Asp Phe Leu Asn Arg Val
            355                 360                 365

Arg Asn Glu Glu Asp Lys Leu Arg Ser Leu Gly Leu Trp Glu Val Pro
370                 375                 380

His Pro Trp Leu Asn Ile Phe Val Pro Gly Ser Arg Ile Gln Asp Phe
385                 390                 395                 400
```

His Asp Gly Val Ile Asn Gly Leu Leu Leu Asn Gln Thr Ser Thr Ser
            405                 410                 415

Gly Val Thr Leu Phe Tyr Pro Thr Asn Arg Asn Lys Trp Asn Asn Arg
            420                 425                 430

Met Ser Thr Met Thr Pro Asp Glu Asp Val Phe Tyr Val Ile Gly Leu
            435                 440                 445

Leu Gln Ser Ala Gly Gly Ser Gln Asn Trp Gln Glu Leu Glu Asn Leu
450                 455                 460

Asn Asp Lys Val Ile Gln Phe Cys Glu Asn Ser Gly Ile Lys Ile Lys
465                 470                 475                 480

Glu Tyr Leu Met His Tyr Thr Arg Lys Glu Asp Trp Val Lys His Phe
            485                 490                 495

Gly Pro Lys Trp Asp Asp Phe Leu Arg Lys Lys Ile Met Phe Asp Pro
            500                 505                 510

Lys Arg Leu Leu Ser Pro Gly Gln Asp Ile Phe Asn
            515                 520

<210> SEQ ID NO 9
<211> LENGTH: 540
<212> TYPE: PRT
<213> ORGANISM: Arabidopsis thaliana

<400> SEQUENCE: 9

Met Asn Arg Glu Met Thr Ser Ser Phe Leu Leu Thr Phe Ala Ile
1               5                   10                  15

Cys Lys Leu Ile Ile Ala Val Gly Leu Asn Val Gly Pro Ser Glu Leu
            20                  25                  30

Leu Arg Ile Gly Ala Ile Asp Val Asp Gly His Phe Thr Val His Pro
            35                  40                  45

Ser Asp Leu Ala Ser Val Ser Ser Asp Phe Gly Met Leu Lys Ser Pro
50                  55                  60

Glu Glu Pro Leu Ala Val Leu His Pro Ser Ser Ala Glu Asp Val Ala
65                  70                  75                  80

Arg Leu Val Arg Thr Ala Tyr Gly Ser Ala Thr Ala Phe Pro Val Ser
            85                  90                  95

Ala Arg Gly His Gly His Ser Ile Asn Gly Gln Ala Ala Gly Arg
            100                 105                 110

Asn Gly Val Val Val Glu Met Asn His Gly Val Thr Gly Thr Pro Lys
            115                 120                 125

Pro Leu Val Arg Pro Asp Glu Met Tyr Val Asp Val Trp Gly Gly Glu
            130                 135                 140

Leu Trp Val Asp Val Leu Lys Lys Thr Leu Glu His Gly Leu Ala Pro
145                 150                 155                 160

Lys Ser Trp Thr Asp Tyr Leu Tyr Leu Thr Val Gly Gly Thr Leu Ser
            165                 170                 175

Asn Ala Gly Ile Ser Gly Gln Ala Phe His His Gly Pro Gln Ile Ser
            180                 185                 190

Asn Val Leu Glu Leu Asp Val Val Thr Gly Lys Gly Glu Val Met Arg
            195                 200                 205

Cys Ser Glu Glu Glu Asn Thr Arg Leu Phe His Gly Val Leu Gly Gly
            210                 215                 220

Leu Gly Gln Phe Gly Ile Ile Thr Arg Ala Arg Ile Ser Leu Glu Pro
225                 230                 235                 240

Ala Pro Gln Arg Val Arg Trp Ile Arg Val Leu Tyr Ser Ser Phe Lys

```
            245                 250                 255
Val Phe Thr Glu Asp Gln Glu Tyr Leu Ile Ser Met His Gly Gln Leu
            260                 265                 270

Lys Phe Asp Tyr Val Glu Gly Phe Val Ile Val Asp Glu Gly Leu Val
            275                 280                 285

Asn Asn Trp Arg Ser Ser Phe Ser Pro Arg Asn Pro Val Lys Ile
290                 295                 300

Ser Ser Val Ser Ser Asn Gly Ser Val Leu Tyr Cys Leu Glu Ile Thr
305                 310                 315                 320

Lys Asn Tyr His Asp Ser Asp Ser Glu Ile Val Asp Gln Glu Val Glu
            325                 330                 335

Ile Leu Met Lys Lys Leu Asn Phe Ile Pro Thr Ser Val Phe Thr Thr
            340                 345                 350

Asp Leu Gln Tyr Val Asp Phe Leu Asp Arg Val His Lys Ala Glu Leu
            355                 360                 365

Lys Leu Arg Ser Lys Asn Leu Trp Glu Val Pro His Pro Trp Leu Asn
            370                 375                 380

Leu Phe Val Pro Lys Ser Arg Ile Ser Asp Phe Asp Lys Gly Val Phe
385                 390                 395                 400

Lys Gly Ile Leu Gly Asn Lys Thr Ser Gly Pro Ile Leu Ile Tyr Pro
                405                 410                 415

Met Asn Lys Asp Lys Trp Asp Glu Arg Ser Ser Ala Val Thr Pro Asp
            420                 425                 430

Glu Glu Val Phe Tyr Leu Val Ala Leu Leu Arg Ser Ala Leu Thr Asp
            435                 440                 445

Gly Glu Glu Thr Gln Lys Leu Glu Tyr Leu Lys Asp Gln Asn Arg Arg
450                 455                 460

Ile Leu Glu Phe Cys Glu Gln Ala Lys Ile Asn Val Lys Gln Tyr Leu
465                 470                 475                 480

Pro His His Ala Thr Gln Glu Glu Trp Val Ala His Phe Gly Asp Lys
                485                 490                 495

Trp Asp Arg Phe Arg Ser Leu Lys Ala Glu Phe Asp Pro Arg His Ile
            500                 505                 510

Leu Ala Thr Gly Gln Arg Ile Phe Gln Asn Pro Ser Leu Ser Leu Phe
            515                 520                 525

Pro Pro Ser Ser Ser Ser Ser Ala Ala Ser Trp
530                 535                 540

<210> SEQ ID NO 10
<211> LENGTH: 533
<212> TYPE: PRT
<213> ORGANISM: Arabidopsis thaliana

<400> SEQUENCE: 10

Met Ser Tyr Leu His Ala Ser Leu Leu Arg Lys Arg Thr Met Leu Ile
1               5                   10                  15

Val Arg Ser Phe Thr Ile Leu Leu Ser Cys Ile Ala Phe Lys Leu
            20                  25                  30

Ala Cys Cys Phe Ser Ser Ile Ser Ser Leu Lys Ala Leu Pro Leu
            35                  40                  45

Val Gly His Leu Glu Phe Glu His Val His Ala Ser Lys Asp Phe
            50                  55                  60

Gly Asn Arg Tyr Gln Leu Ile Pro Leu Ala Val Leu His Pro Lys Ser
65                  70                  75                  80
```

-continued

Val Ser Asp Ile Ala Ser Thr Ile Arg His Ile Trp Met Met Gly Thr
                    85                  90                  95

His Ser Gln Leu Thr Val Ala Ala Arg Gly Arg Gly His Ser Leu Gln
            100                 105                 110

Gly Gln Ala Gln Thr Arg His Gly Ile Val Ile His Met Glu Ser Leu
        115                 120                 125

His Pro Gln Lys Leu Gln Val Tyr Ser Val Asp Ser Pro Ala Pro Tyr
    130                 135                 140

Val Asp Val Ser Gly Gly Glu Leu Trp Ile Asn Ile Leu His Glu Thr
145                 150                 155                 160

Leu Lys Tyr Gly Leu Ala Pro Lys Ser Trp Thr Asp Tyr Leu His Leu
                165                 170                 175

Thr Val Gly Gly Thr Leu Ser Asn Ala Gly Ile Ser Gly Gln Ala Phe
            180                 185                 190

Arg His Gly Pro Gln Ile Ser Asn Val His Gln Leu Glu Ile Val Thr
        195                 200                 205

Gly Lys Gly Glu Ile Leu Asn Cys Thr Lys Arg Gln Asn Ser Asp Leu
    210                 215                 220

Phe Asn Gly Val Leu Gly Gly Leu Gly Gln Phe Gly Ile Ile Thr Arg
225                 230                 235                 240

Ala Arg Ile Ala Leu Glu Pro Ala Pro Thr Met Val Lys Trp Ile Arg
                245                 250                 255

Val Leu Tyr Leu Asp Phe Ala Ala Phe Ala Lys Asp Gln Glu Gln Leu
            260                 265                 270

Ile Ser Ala Gln Gly His Lys Phe Asp Tyr Ile Glu Gly Phe Val Ile
        275                 280                 285

Ile Asn Arg Thr Gly Leu Leu Asn Ser Trp Arg Leu Ser Phe Thr Ala
    290                 295                 300

Glu Glu Pro Leu Glu Ala Ser Gln Phe Lys Phe Asp Gly Arg Thr Leu
305                 310                 315                 320

Tyr Cys Leu Glu Leu Ala Lys Tyr Leu Lys Gln Asp Asn Lys Asp Val
                325                 330                 335

Ile Asn Gln Glu Val Lys Glu Thr Leu Ser Glu Leu Ser Tyr Val Thr
            340                 345                 350

Ser Thr Leu Phe Thr Thr Glu Val Ala Tyr Glu Ala Phe Leu Asp Arg
        355                 360                 365

Val His Val Ser Glu Val Lys Leu Arg Ser Lys Gly Gln Trp Glu Val
    370                 375                 380

Pro His Pro Trp Leu Asn Leu Leu Val Pro Arg Ser Lys Ile Asn Glu
385                 390                 395                 400

Phe Ala Arg Gly Val Phe Gly Asn Ile Leu Thr Asp Thr Ser Asn Gly
                405                 410                 415

Pro Val Ile Val Tyr Pro Val Asn Lys Ser Lys Trp Asp Asn Gln Thr
            420                 425                 430

Ser Ala Val Thr Pro Glu Glu Val Phe Tyr Leu Val Ala Ile Leu
        435                 440                 445

Thr Ser Ala Ser Pro Gly Ser Ala Gly Lys Asp Gly Val Glu Glu Ile
    450                 455                 460

Leu Arg Arg Asn Arg Arg Ile Leu Glu Phe Ser Glu Ala Gly Ile
465                 470                 475                 480

Gly Leu Lys Gln Tyr Leu Pro His Tyr Thr Thr Arg Glu Glu Trp Arg
                485                 490                 495

Ser His Phe Gly Asp Lys Trp Gly Glu Phe Val Arg Arg Lys Ser Arg

```
            500                 505                 510
Tyr Asp Pro Leu Ala Ile Leu Ala Pro Gly His Arg Ile Phe Gln Lys
                515                 520                 525

Ala Val Ser Tyr Ser
            530

<210> SEQ ID NO 11
<211> LENGTH: 524
<212> TYPE: PRT
<213> ORGANISM: Arabidopsis thaliana

<400> SEQUENCE: 11

Met Ile Ala Tyr Ile Glu Pro Tyr Phe Leu Glu Asn Asp Ala Glu Ala
1               5                   10                  15

Ala Ser Ala Ala Thr Ala Ala Gly Lys Ser Thr Asp Gly Val Ser Glu
            20                  25                  30

Ser Leu Asn Ile Gln Gly Glu Ile Leu Cys Gly Gly Ala Ala Ala Asp
        35                  40                  45

Ile Ala Gly Arg Asp Phe Gly Met Asn Cys Val Lys Pro Leu Ala
    50                  55                  60

Val Val Arg Pro Val Gly Pro Glu Asp Ile Ala Gly Ala Val Lys Ala
65                  70                  75                  80

Ala Leu Arg Ser Asp Lys Leu Thr Val Ala Ala Arg Gly Asn Gly His
                85                  90                  95

Ser Ile Asn Gly Gln Ala Met Ala Glu Gly Gly Leu Val Val Asp Met
            100                 105                 110

Ser Thr Thr Ala Glu Asn His Phe Glu Val Gly Tyr Leu Ser Gly Gly
        115                 120                 125

Asp Ala Thr Ala Phe Val Asp Val Ser Gly Gly Ala Leu Trp Glu Asp
    130                 135                 140

Val Leu Lys Arg Cys Val Ser Glu Tyr Gly Leu Ala Pro Arg Ser Trp
145                 150                 155                 160

Thr Asp Tyr Leu Gly Leu Thr Val Gly Gly Thr Leu Ser Asn Ala Gly
                165                 170                 175

Val Ser Gly Gln Ala Phe Arg Tyr Gly Pro Gln Thr Ser Asn Val Thr
            180                 185                 190

Glu Leu Asp Val Val Thr Gly Asn Gly Asp Val Val Thr Cys Ser Glu
        195                 200                 205

Ile Glu Asn Ser Glu Leu Phe Phe Ser Val Leu Gly Gly Leu Gly Gln
    210                 215                 220

Phe Gly Ile Ile Thr Arg Ala Arg Val Leu Leu Gln Pro Ala Pro Asp
225                 230                 235                 240

Met Val Arg Trp Ile Arg Val Val Tyr Thr Glu Phe Asp Glu Phe Thr
                245                 250                 255

Gln Asp Ala Glu Trp Leu Val Ser Gln Lys Asn Glu Ser Ser Phe Asp
            260                 265                 270

Tyr Val Glu Gly Phe Val Phe Val Asn Gly Ala Asp Pro Val Asn Gly
        275                 280                 285

Trp Pro Thr Val Pro Leu His Pro Asp His Glu Phe Asp Pro Thr Arg
    290                 295                 300

Leu Pro Gln Ser Cys Gly Ser Val Leu Tyr Cys Leu Glu Leu Gly Leu
305                 310                 315                 320

His Tyr Arg Asp Ser Asp Ser Asn Ser Thr Ile Asp Lys Arg Val Glu
                325                 330                 335
```

```
Arg Leu Ile Gly Arg Leu Arg Phe Asn Glu Gly Leu Arg Phe Glu Val
                340                 345                 350

Asp Leu Pro Tyr Val Asp Phe Leu Leu Arg Val Lys Arg Ser Glu Glu
            355                 360                 365

Ile Ala Lys Glu Asn Gly Thr Trp Glu Thr Pro His Pro Trp Leu Asn
        370                 375                 380

Leu Phe Val Ser Lys Arg Asp Ile Gly Asp Phe Asn Arg Thr Val Phe
385                 390                 395                 400

Lys Glu Leu Val Lys Asn Gly Val Asn Gly Pro Met Leu Val Tyr Pro
                405                 410                 415

Leu Leu Arg Ser Arg Trp Asp Asp Arg Thr Ser Val Val Ile Pro Glu
            420                 425                 430

Glu Gly Glu Ile Phe Tyr Ile Val Ala Leu Leu Arg Phe Val Pro Pro
        435                 440                 445

Cys Ala Lys Val Ser Ser Val Glu Lys Met Val Ala Gln Asn Gln Glu
    450                 455                 460

Ile Val His Trp Cys Val Lys Asn Gly Ile Asp Tyr Lys Leu Tyr Leu
465                 470                 475                 480

Pro His Tyr Lys Ser Gln Glu Glu Trp Ile Arg His Phe Gly Asn Arg
                485                 490                 495

Trp Ser Arg Phe Val Asp Arg Lys Ala Met Phe Asp Pro Met Ala Ile
            500                 505                 510

Leu Ser Pro Gly Gln Lys Ile Phe Asn Arg Ser Leu
        515                 520

<210> SEQ ID NO 12
<211> LENGTH: 132
<212> TYPE: PRT
<213> ORGANISM: Arabidopsis thaliana

<400> SEQUENCE: 12

Met Leu Gly Leu Gly Val Asp Arg Leu Gln Ala Asp Ile Asn Arg Leu
1               5                   10                  15

Leu Ala Ser Leu Phe His Gln Gly Val Leu Asp Glu Gln Phe Leu Gln
            20                  25                  30

Leu Gln Gln Leu Gln Asp Glu Thr Ser Pro Asn Phe Val Met Asp Arg
        35                  40                  45

Glu Phe Ser Asp Tyr Lys Lys Ile Gly Leu His Leu Asn Gln Leu Val
    50                  55                  60

Gly Ser Ser Ser Ile Gly Ala Arg Arg Val Arg Asn Val Cys Val
65                  70                  75                  80

Ala Phe Arg Ser Ala Ser Glu Leu Ser Asn Arg Pro Gly Cys Leu Arg
                85                  90                  95

Gly Leu Glu Val Val Glu His Glu Tyr His Tyr Leu Lys Asn Met Met
            100                 105                 110

His Glu Leu Phe Gln Leu Glu Gln Gln Arg Ile Leu Ala Ala Gly Val
        115                 120                 125

Arg Tyr Pro Met
    130

<210> SEQ ID NO 13
<211> LENGTH: 399
<212> TYPE: DNA
<213> ORGANISM: Arabidopsis thaliana

<400> SEQUENCE: 13
```

```
atgttggggt tgggtgtgga ccggcttcaa gccgacatca accggctcct agcctctctt      60
ttccaccagg gagtgctgga cgagcagttc ttgcagcttc agcagcttca agatgagact     120
tcaccaaact ttgtgatgga tagagaattc tcggactata agaaaatagg attacacctg     180
aatcagctgg tgggaagcag ttcaagcatt ggtgctcgta gggttcgtaa cgtctgcgtt     240
gcctttcgtt ctgcttccga gcttagcaac cgcccagggt gcttgagagg actggaggta     300
gtagagcatg agtatcatta cctcaagaac atgatgcatg aactcttcca gctggagcag     360
cagagaatat tagctgcagg agtcagatat ccaatgtaa                            399

<210> SEQ ID NO 14
<211> LENGTH: 574
<212> TYPE: DNA
<213> ORGANISM: Arabidopsis thaliana

<400> SEQUENCE: 14
gaagcaagac ctgttcacat tagtaaaaac aaatatatag aaagaggaaa gattgaagcg      60
gaaaacggga caagacgggt gtgccgttgt ggatgttggg gttgggtgtg gaccggcttc     120
aagccgacat caaccggctc ctagcctctc ttttccacca gggagtgctg gacgagcagt     180
tcttgcagct tcagcagctt caagatgaga cttcaccaaa ctttgtgatg gatagagaat     240
tctcggacta taagaaaata ggattacacc tgaatcagct ggtgggaagc agttcaagca     300
ttggtgctcg taggggttcgt aacgtctgcg ttgcctttcg ttctgcttcc gagcttagca     360
accgcccagg gtgcttgaga ggactggagg tagtagagca tgagtatcat tacctcaaga     420
acatgatgca tgaactcttc cagctggagc agcagagaat attagctgca ggagtcagat     480
atccaatgta aaattagaat tttgtcataa aaatcagaga aaacctaatt agtgtgtgat     540
gatagtgtgt tataagctac cgaagcgaaa ccct                                 574
```